United States Patent [19]

Gabay et al.

[11] Patent Number: 5,338,724
[45] Date of Patent: * Aug. 16, 1994

[54] ANTIMICROBIAL PROTEINS, COMPOSITIONS CONTAINING SAME AND USES THEREOF

[75] Inventors: Joelle E. Gabay, New York; Carl E. Nathan, Larchmont, both of N.Y.

[73] Assignees: Cornell Research Foundation, Inc.; Rockefeller University, both of New York, N.Y.

[*] Notice: The portion of the term of this patent subsequent to Feb. 11, 2009 has been disclaimed.

[21] Appl. No.: 835,725

[22] Filed: Feb. 11, 1992

Related U.S. Application Data

[60] Division of Ser. No. 125,684, Nov. 25, 1987, Pat. No. 5,087,569, which is a continuation-in-part of Ser. No. 106,524, Oct. 6, 1987, Pat. No. 5,126,257, which is a continuation-in-part of Ser. No. 935,509, Nov. 26, 1986, abandoned.

[51] Int. Cl.$^5$ ............................................. A61K 37/02
[52] U.S. Cl. .......................................... 514/12; 514/2; 530/350; 530/380; 530/386; 930/10; 930/190; 930/290
[58] Field of Search ................. 530/350, 380, 386; 514/12, 13, 21, 14; 435/212; 930/10, 190, 290

[56] References Cited

U.S. PATENT DOCUMENTS

| | | | |
|---|---|---|---|
| 4,639,435 | 1/1987 | Fujii et al. | 514/11 |
| 4,755,383 | 7/1988 | Fujii et al. | 424/94.63 |
| 5,087,569 | 2/1992 | Gabay et al. | 435/212 |

OTHER PUBLICATIONS

Heck et al. 1986, Anal. Biochem. 158, 217–227.
Starkey et al. 1976, Biochem. J. 155, 255–263.
Ganz, T., et al., *J. Clin. Invest.* vol. 76, pp. 1427–1435 (1985).
Heck, L. W., et al., *Anal. Biochem.* vol. 149, pp. 153–162 (1985).
Odeberg, H. and Olsson, I., *J. Clin. Invest.* vol. 56, pp. 1118–1124, (1974).
Olsson, I. and Venge, P., *Blood* vol. 44, pp. 235–246 (1974).
Salvesen, G., et al., *Biochemistry* vol. 26, pp. 2289–2293, (1987).
Selsted, M. E., et al., *J. Clin. Invest.* vol. 76, pp. 1436–1439 (1985).
Selsted, M. E., et al., *J. Biol. Chem.* vol. 8, pp. 4579–4584 (1985).
Selsted, M. E., et al., *Infect. & Immun.*, vol. 45 (1) pp. 150–154 (1984).
Shafer, W. M., et al., *Infect. & Immun.*, vol. 45 (1), pp. 29–35 (1984).

*Primary Examiner*—Christopher S. F. Low
*Attorney, Agent, or Firm*—John P. White

[57] ABSTRACT

The present invention provides a composition of matter useful as an antimicrobial agent. This composition of matter comprises at least two polypeptides selected from the group consisting of human polymorphonuclear leukocyte, polypeptides having on apparent molecular weights of about 3,500 daltons, about 13,000 daltons, about 18,000 daltons, about 29,000 daltons, and about 54,000 daltons. The composition of matter has respiratory burst-independent, antimicrobial activity for bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M. Methods for preparing this composition of matter are also provided.

Further provided are purified polypeptides useful as antimicrobial agents, and methods for producing these polypeptides.

7 Claims, 29 Drawing Sheets

FIGURE 14

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1  | X | Y | X | R | I | P | A | X | I | A | G | E | R | R | Y | G | T | X | I | X |
| 2  | V | X | S | X | R | L | V | F | X | R | R | T | E | L | R | V | G | N | N | L |
| 3  | X | P | P | Q | F | T | X | A | Q | X | F | A | I | Q | X | I | X | L | N | P |
| 4  | I | I | G | G | R | E | S | R | P | H | S | R | H | Y | M | A | Y | L | Q | I |
| 5a | K | V | F | E | R | X | E | L | A | R | T | L | P | R | L | A | X | F | T | X |
| 5b | T | C | R | Y | L | L | V | R | S | L | Q | T | K | S | Q | A | S | I | Q | N |
| 6  | I | V | G | G | R | K | A | R | P | R | Q | F | F | F | L | D | S | L | D | M |
| 7  | I | V | G | G | H | E | A | X | X | P | S | F | P | Y | M | V | A | S | Q | L |
| 8  | I | V | G | G | R | R | A | R | P | H | A | D | P | F | D | A | X | F | Q | Q |
| 9a | V | N | P | G | V | V | V | R | I | S | Q | K | K | L | D | Y | X | S | T | X |
| 9b | T | C | R | Y | L | L | V | R | S | L | Q | T | F | S | Q | A | X | F | T | X |

| | 22 | 24 | 26 | 28 | 30 | 32 | 34 | 36 | 38 | 40 |
|---|---|---|---|---|---|---|---|---|---|---|
| 1  | Q | V | S | Y | D |   |   |   |   |   |
| 2  | I | A | F | L | X |   |   |   |   |   |
| 3  |   |   |   |   |   |   |   |   |   |   |
| 4  | Q | P | T | X | S | H | F | N | Y | I |
| 5a | R | Y | R | N | L | I | N | I | Y | R |
| 5b | R | H | G | L | V | H | F | P | L |   |
| 6  | G | A | F | X | X | I | K | D | Y | I |
| 7  |   |   |   |   |   |   |   |   |   |   |
| 8  |   |   |   |   |   |   |   |   |   |   |
| 9a | T | A | L | X | K | H | H | P | N |   |
| 9b | R | Y | R | N | L | I | N | I | Y | R |

FIGURE 20A

| FIGURE 20A |
|---|
| FIGURE 20B |
| FIGURE 20C |
| FIGURE 20D |

```
         60         70         80         90        100        110
          |          |          |          |          |          |
ATGAAACTCCCCCTACTTCTGGCTCTCTTCTATTGGGGCAGTTTCTGCTCTTCATCTAAGG
                                        10                    20
                                         |                     |
METLysLeuProLeuLeuLeuAlaLeuLeuPheGlyAlaValSerAlaLeuHisLeuArg 120        130        140        150        160        170
          |          |          |          |          |          |
TCTGAGACTTCCACCTTTGAGACCCCTTTGGTGCTAAGACGCTGCCTGAGGATGAGGAGA
                   30                                          40
                    |                                           |
SerGluThrSerThrPheGluThrProLeuValLeuArgArgCysLeuArgMETArgArg 180        190        200        210        220        230
          |          |          |          |          |          |
CACCAGAGCAGGAGATGGAGGAGACCTTGCAGGAGCTGAGGAAGAGGAGGAGTGGGGC
                              50                              60
                               |                               |
HisGlnSerArgArgTrpArgArgProCysArgGluLeuGluGluGluGluGluTrpGly
```

FIGURE 20B

```
240          250          260          270          280          290
 |            |            |            |            |            |
TCTGGAAGTGAAGATGCCTCCAAGAAAGATGGGGCTGTTGAGTCTATCTCAGTGCCAGAT
                                                    70            80
                                                    |             |
SerGlySerGluAspAlaSerLysLysAspGlyAlaValGluSerIleSerValProAsp 300          310          320          330          340          350
 |            |            |            |            |            |
ATGGTGGACAAAAACCTTACGTGTCCTGAGGAAGAGGACACAGTAAAAGTGGTGGGCATC
                                        90                       100
                                        |                         |
METValAspLysAsnLeuThrCysProGluGluAspThrValLysValValGlyIle 360          370          380          390          400          410
 |            |            |            |            |            |
CCTGGGGCGCCAGACCTGCCGCTACCTCCTGGTGAGAAGTCTTCACACGTTTAGTCAAGCT
                            110                                  120
                            |                                     |
ProGlyArgGlnThrCysArgTyrLeuLeuValArgSerLeuGlnThrPheSerGlnAla
```

FIGURE 20C

```
         420         430         440         450         460         470
          |           |           |           |           |           |
TGGTTTACTTGCCGGAGGTGCTACAGGGCAACCTGGTTTCCATCCACAACTTCAATATT
                                                                       |
                                                                      140
TrpPheThrCysArgArgCysTyrArgGlyAsnLeuValSerIleHisAsnPheAsnIle 480         490         500         510         520         530
          |           |           |           |           |           |
AATTATCGAATCCATGTTCTCTGTCAGCGCGCTCAACCAGGTCAAGTCTGGATTGGAGGCA
                                                                       |
                                                                      160
AsnTyrArgIleHisValLeuSerAlaArgSerThrArgValLysSerGlyLeuGluAla 540         550         560         570         580         590
          |           |           |           |           |           |
GGATCACAGGCTCGGGTCGCTGCAGACGCTTTCAGTGGGTTGACGGCAGCCGCTGGAACT
                                                                       |
                                                                      180
GlySerGlnAlaArgValAlaAlaAlaAspAlaPheSerGlyLeuThrAlaAlaAlaGlyThr
```

FIGURE 20D

```
600        610        620        630        640        650
 |          |          |          |          |          |
TTGCGTACTGGGCTGCTCACCAGCCTGGTCCCGGGTGGTCACTGCGTGGCCCTGTGTAC
                              190                    200
                               |                      |
LeuArgThrGlyLeuLeuThrSerLeuValProArgTrpSerLeuArgGlyProValTyr 660        670        680        690        700        710
 |          |          |          |          |          |
CCGAGGAGGCTACTGGCGTCGAGCCACTGCCTCAGAAGCCTTCCTTTCATCTGTTCCTAC
                              210                    220
                               |                      |
ProArgArgLeuLeuAlaSerSerHisCysLeuArgSerLeuProPheIleCysSerTyr

TGA
 |
```

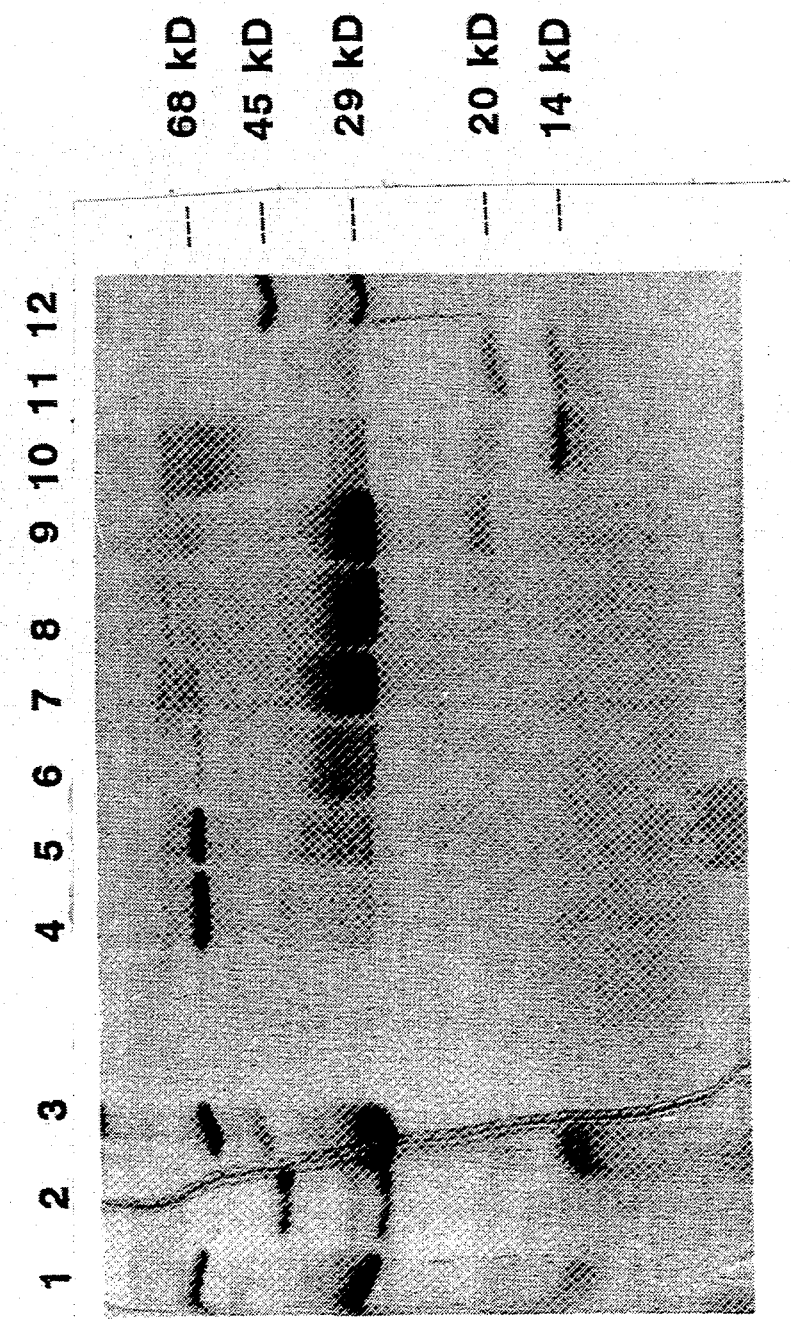

ANTIMICROBIAL PROTEINS, COMPOSITIONS CONTAINING SAME AND USES THEREOF

This invention was made with government support under grant numbers CA 22090 and CA 43610 from the National Cancer Institute and grant numbers AI 07012 and AI 20516 from the U.S. Public Health Service. The U.S. Government has certain rights in the invention.

This application is a division application of U.S. Ser. No. 125,684, filed Nov. 25, 1987, now U.S. Pat. No. 5,087,569, issued Feb. 11, 1992, which is continuation-in-part of U.S. Ser. No. 106,525, filed Oct. 6, 1987, now U.S. Pat. No. 5,126,257 issued Jun. 30, 1992, which is a continuation-in-part of U.S. Ser. No. 935,509, filed Nov. 26, 1986, abandoned, the contents of both of which are hereby incorporated by reference into the subject application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Granulocytes are key components of at least two host defense systems against opportunistic microbial infection. In one of these systems, the polymorphonuclear leukocytes (PMNs) produce reactive oxygen intermediates which directly or indirectly destroy invading microorganisms. The other system depends on mechanisms which are independent of the respiratory burst (1–3). Neutrophil-derived proteins have long been implicated as components of this respiratory burst-independent microbicidal pathway (4–6). One group of low molecular weight (less than 4 kD) human neutrophil antibiotic peptides, called defensins, have been sequenced and shown to be localized immunohistochemically to azurophil granules (7). These peptides demonstrate in vitro antibacterial, antifungal, and antiviral effects which are highly dependent on many factors, including pH, ionic strength, and calcium or magnesium concentration. Additionally, the mode of action of these peptides and their actual contribution to in vivo antimicrobial activity are a matter of debate.

SUMMARY OF THE INVENTION

The present invention provides a composition of matter useful as an antimicrobial agent. This composition of matter comprises at least two polypeptides selected from the group consisting of human polymorphonuclear leukocyte polypeptides having apparent molecular weights of about 3,500 daltons, about 13,000 daltons, about 18,000 daltons, about 29,000 daltons, and about 54,000 daltons. The composition of matter has respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M.

The present invention also provides a method of preparing a composition of matter useful as an antimicrobial agent. This method comprises substantially separating polymorphonuclear leukocytes from blood so as to obtain a polymorphonuclear leukocyte-enriched preparation. The polymorphonuclear leukocyte-enriched preparation is suspended in a suitable buffer, the resulting suspension is treated with a suitable protease inhibitor, and the suspended cells are treated under lysing conditions so as to obtain a suspension of lysed leukocytes. The suspension of lysed leukocytes is treated with a suitable chelating agent and the treated suspension then centrifuged so as to obtain a nuclei/unbroken cell phase and a postnuclear supernatant. The postnuclear supernatant is recovered and fractionated on a density gradient and the fraction which includes azurophil granules is collected and suspended in a buffer which has a pH of about 7.0. The resulting azurophil granule suspension is treated with a reagent having a pH less than about 8.0 and capable of solubilizing azurophil membrane proteins. The treated suspension is separated into a solid phase and a supernatant and the supernatant is then recovered, and thereby the composition of matter useful as an antimicrobial agent is obtained.

The invention also provides a purified polypeptide useful as an antimicrobial agent. This polypeptide comprises a human polymorphonuclear leukocyte polypeptide having a predicted molecular weight of 24,823 daltons and the amino acid sequence shown in FIG. 20, or a fragment derived therefrom.

The present invention further provides another purified polypeptide useful as an antimicrobial agent. This polypeptide comprises a human polymorphonuclear leukocyte polypeptide having an apparent molecular weight of about 18,000 daltons.

Further provided is a purified polypeptide useful as an antimicrobial agent which comprises a human polymorphonuclear leukocyte polypeptide having an apparent molecular weight of about 54,000 daltons. The polypeptide has respiratory burst-independent, antibacterial activity at a pH from about 5.0 to about 8.0, at calcium ion concentrations up to about 10 mM, and at sodium chloride concentrations up to about 0.3M.

Also provided is a purified polypeptide useful as an antimicrobial agent which comprises a human polymorphonuclear leukocyte polypeptide having an apparent molecular weight of about 29,000 daltons, respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M.

A purified human polymorphonuclear polypeptide useful as an antimicrobial agent and having an apparent molecular weight of about 25,000 daltons is further provided by the present invention. This polypeptide has respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M.

BRIEF DESCRIPTION OF THE FIGURES

FIG. 1(B) Profile of bactericidal activity. Each fraction was extracted with 0.05M glycine-HCl pH 2.0, centrifuged at 10,000× g for 20 minutes and the supernatant incubated with *E. coli* K12, at a protein concentration of 5 micrograms/ml. The percentage of bacteria killed after 30 minutes incubation at 37° C. is presented here.

FIG. 1C shows the amount of protein from purified azurophils (●) and purified specific granules (Δ) necessary to produce 50% reduction in bacterial colony-forming units ($LD_{50}$).

Solid bars = bactericidal activity profile;

Cross-hatched bars = fungicidal activity profile.

Figure 3:
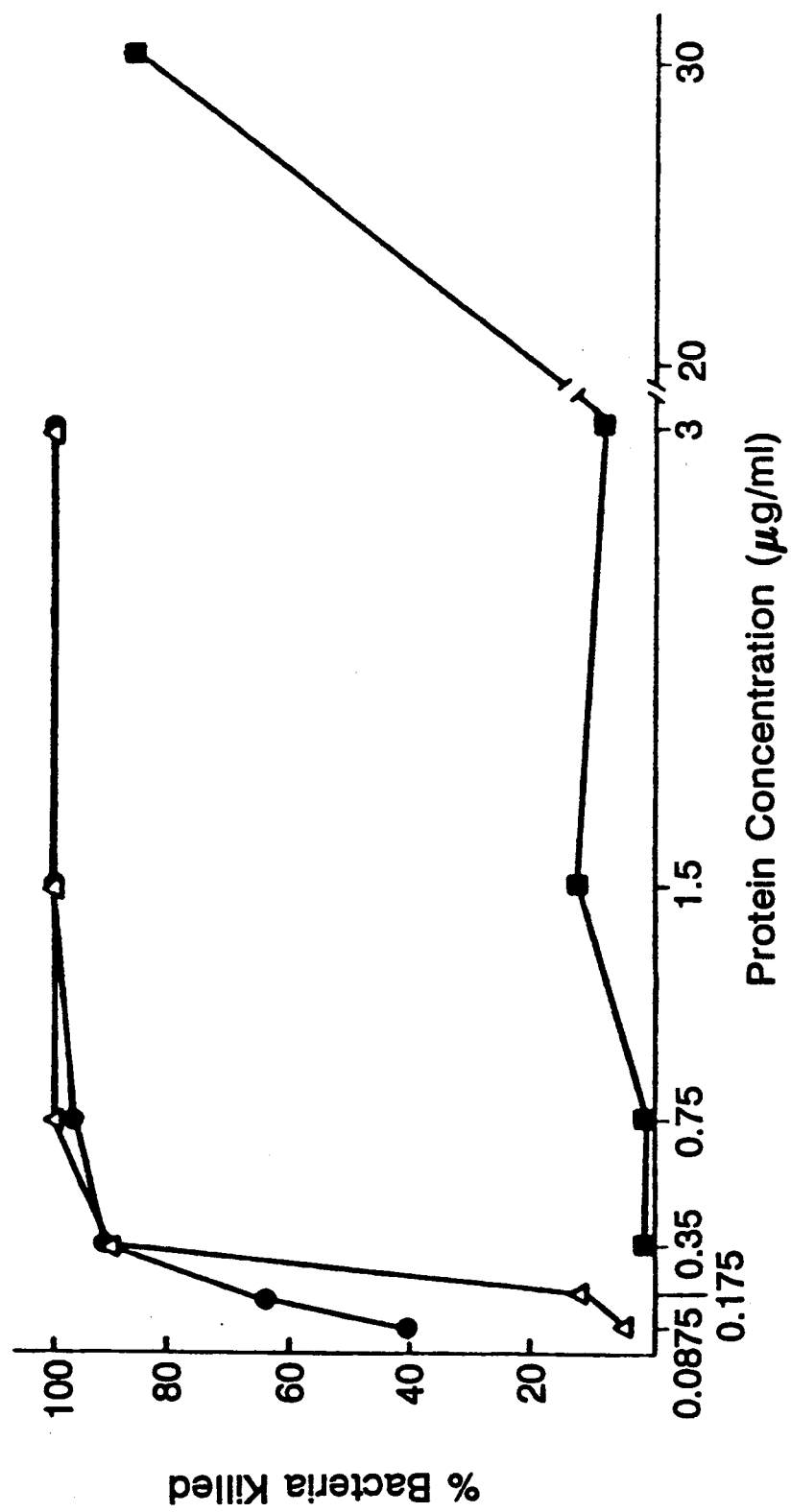

FIG. 3. Membrane association of an azurophil derived bactericidal factor (ADBF)

Isolated azurophil granules in relaxation buffer (pH 7.3, see Materials and Methods) were disrupted by freeze-thaw/sonication and centrifuged. The supernatant (■), the pelleted material (●) and the total granules (Δ) were extracted at pH 2.0 and tested for bactericidal activity.

Figure 4:
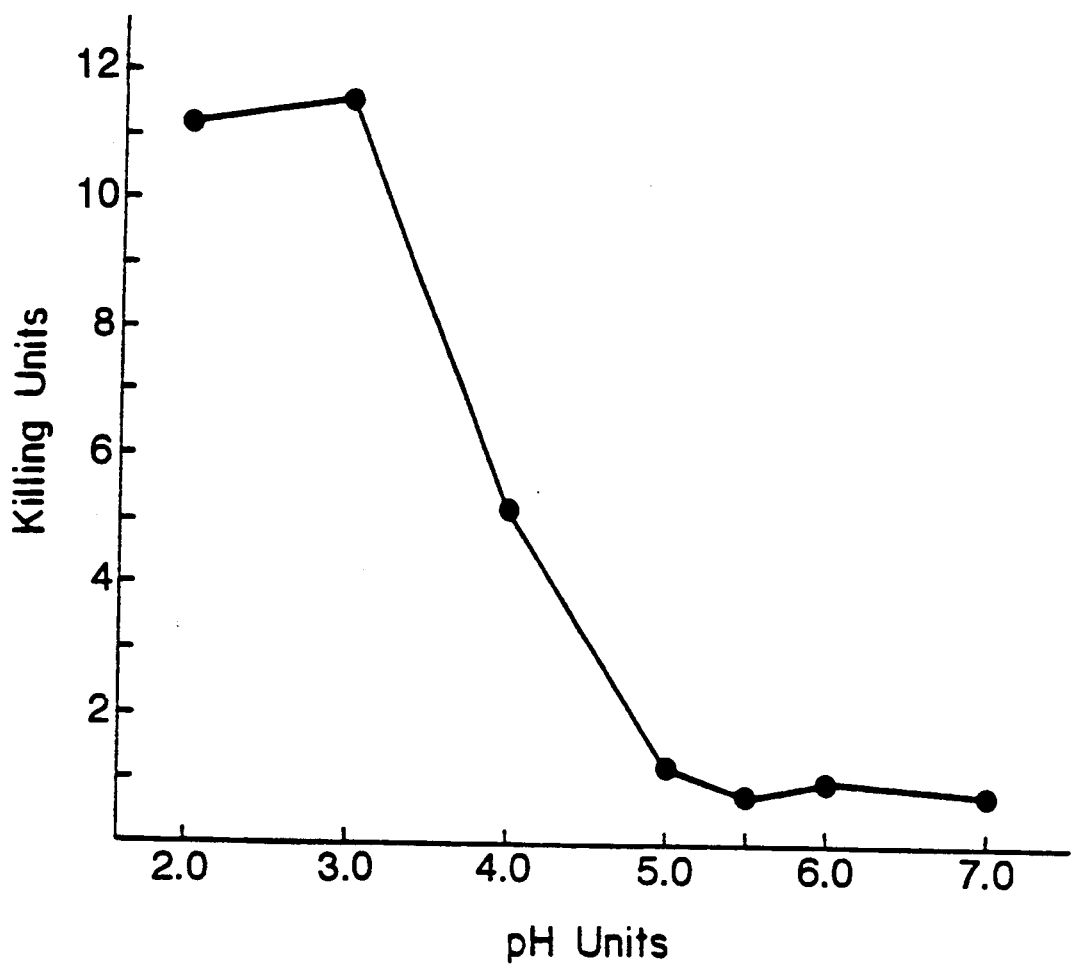

FIG. 4. Effect of pH on the extraction of a bactericidal factor from azurophil granule membranes Aliquots of azurophil membranes were added to various buffer systems (0.05M): glycine, pH 2.0–3.0; citrate, pH 4.0–6.0; phosphate, pH 7.0. After incubation at 25° C. for 40 minutes, the suspensions were centrifuged at 10,000× g for 20 minutes and the supernatants assayed for protein content and bactericidal activity. Killing units (K.U.) correspond to the reciprocal of the number of micrograms/ml of protein necessary to kill $10^5$ bacteria in 30 minutes at 37° C. In each case, the bactericidal assay was conducted in 0.05M citrate buffer, pH 5.5.

Figure 5:
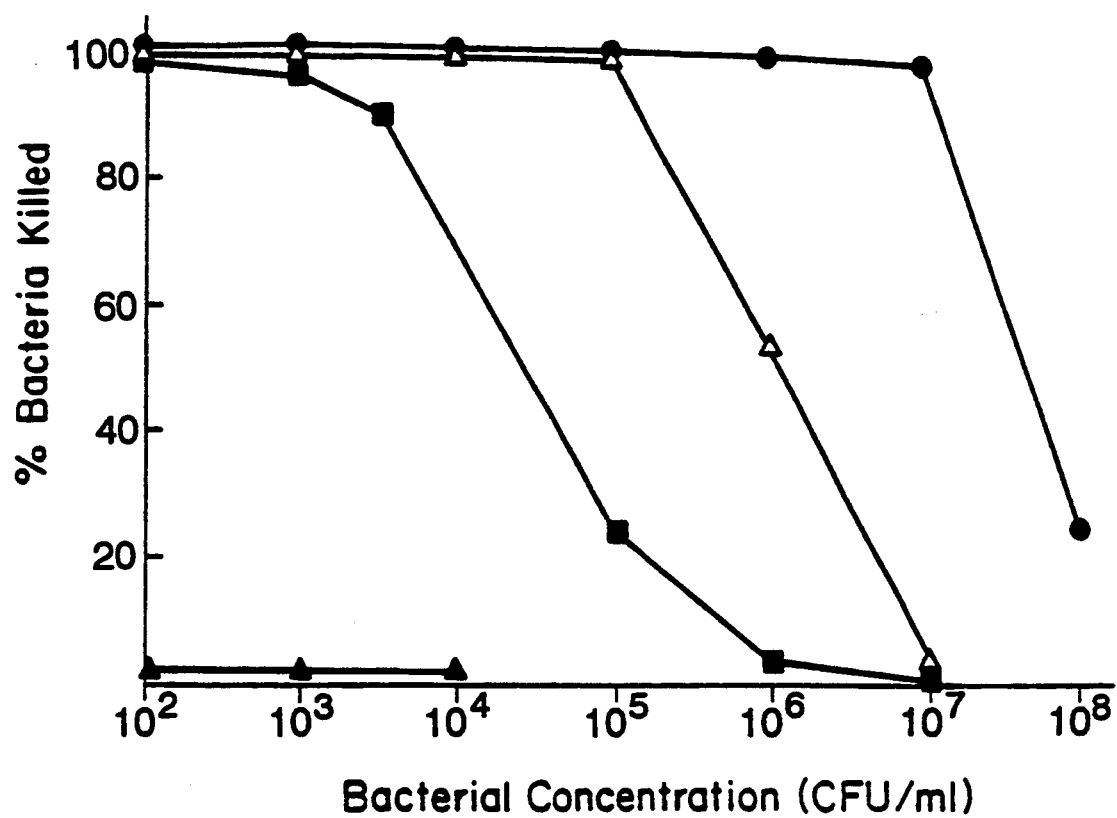

FIG. 5. Bactericidal activity of azurophil granule extract on increasing concentrations of bacteria Granule extract was prepared as described in Materials and Methods. 30 micrograms/ml (●), 3 micrograms/ml (Δ), 0.3 micrograms/ml (■), or 0.03 micrograms/ml (▲) of the azurophil extract were added for each bacterial concentration tested.

Figure 6:
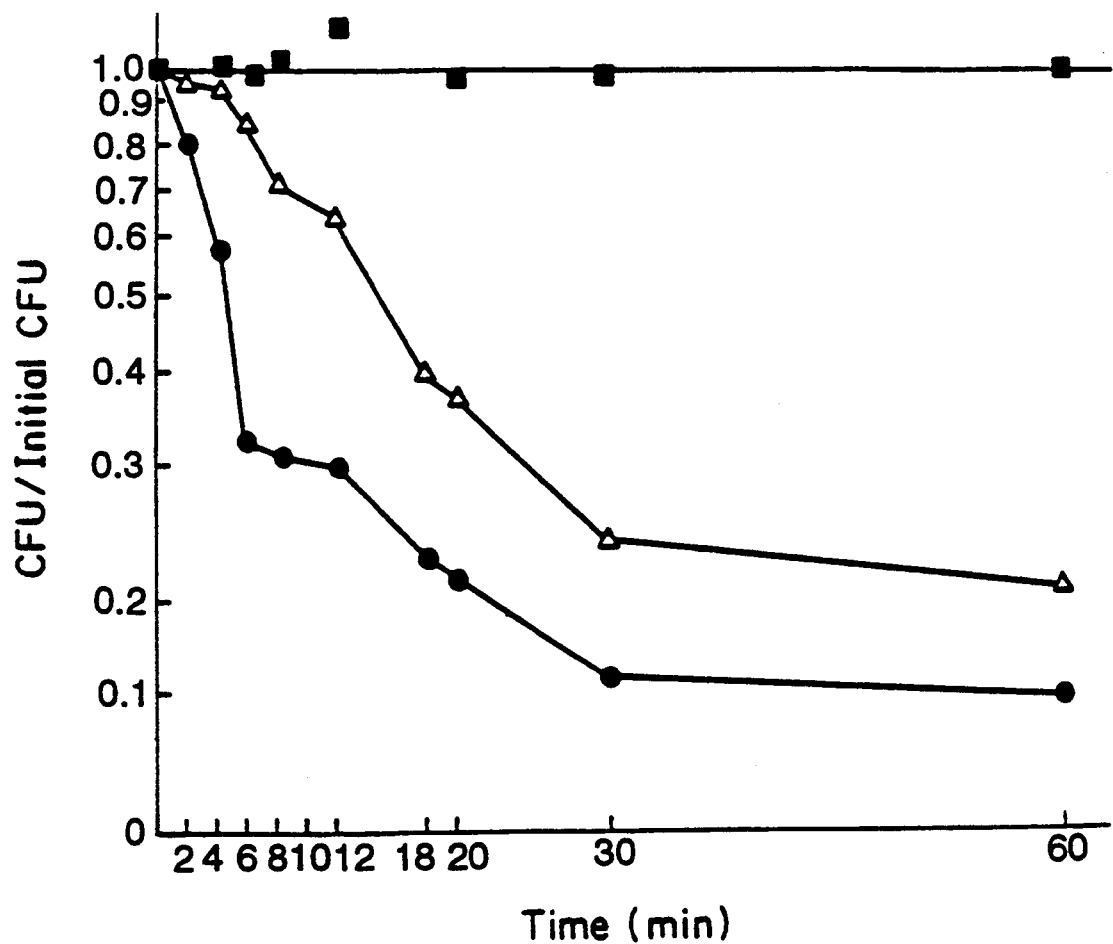

FIG. 6. Kinetics of bactericidal activity of an azurophil-derived bactericidal factor

*E. coli* K12 cells ($2\times 10^5$ CFU/ml) were incubated with 1.4 micrograms/ml (●) or 0.7 micrograms/ml (Δ) of azurophil granule extract in 0.05M citrate buffer pH 5.5 and with citrate buffer alone (■).

Figure 7:
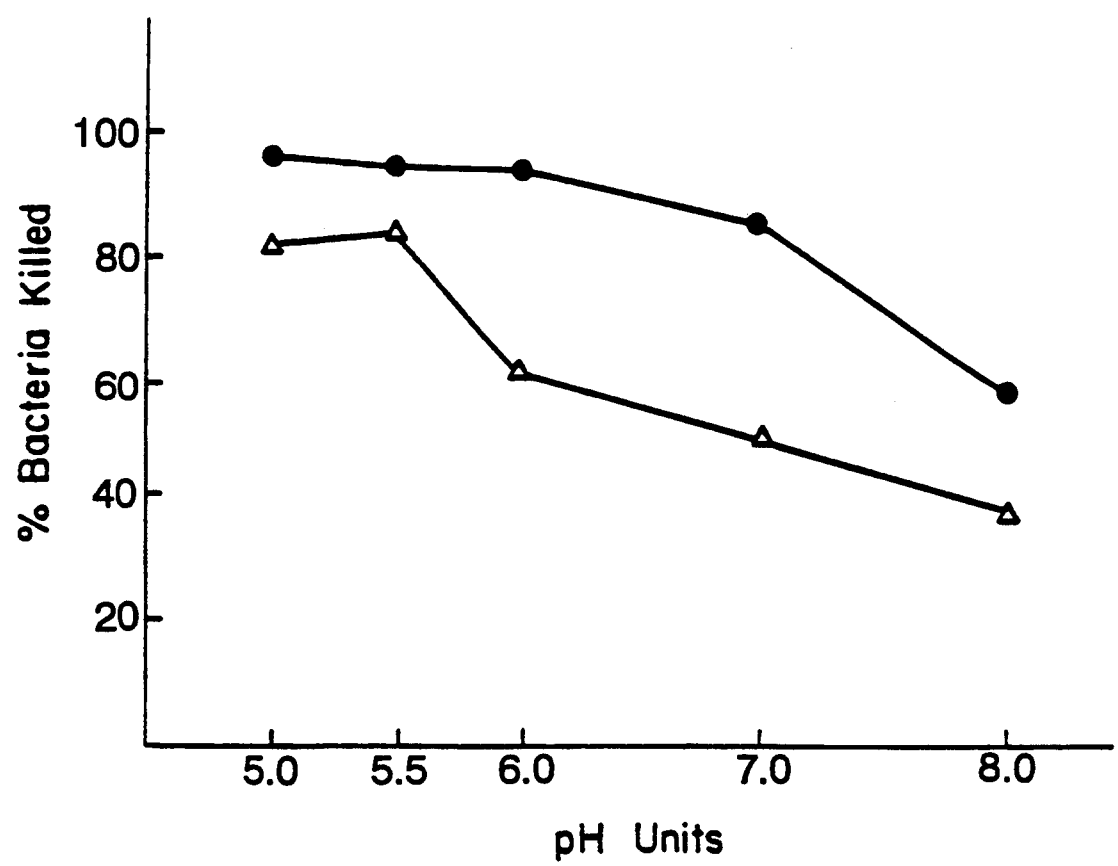

FIG. 7. Effect of pH on bactericidal activity of an azurophil-derived bactericidal factor

*E. coli* K12 cells ($2.5\times 10^5$ CFU/ml) were incubated for 30 minutes at 37° C. with 2.8 micrograms/ml (●) or 0.7 micrograms/ml (Δ) of azurophil granule extract in citrate buffer pH 5 and 5.5 and sodium phosphate or sodium phosphate-citrate buffer pH 6.0 to 8.0.

Figure 8:
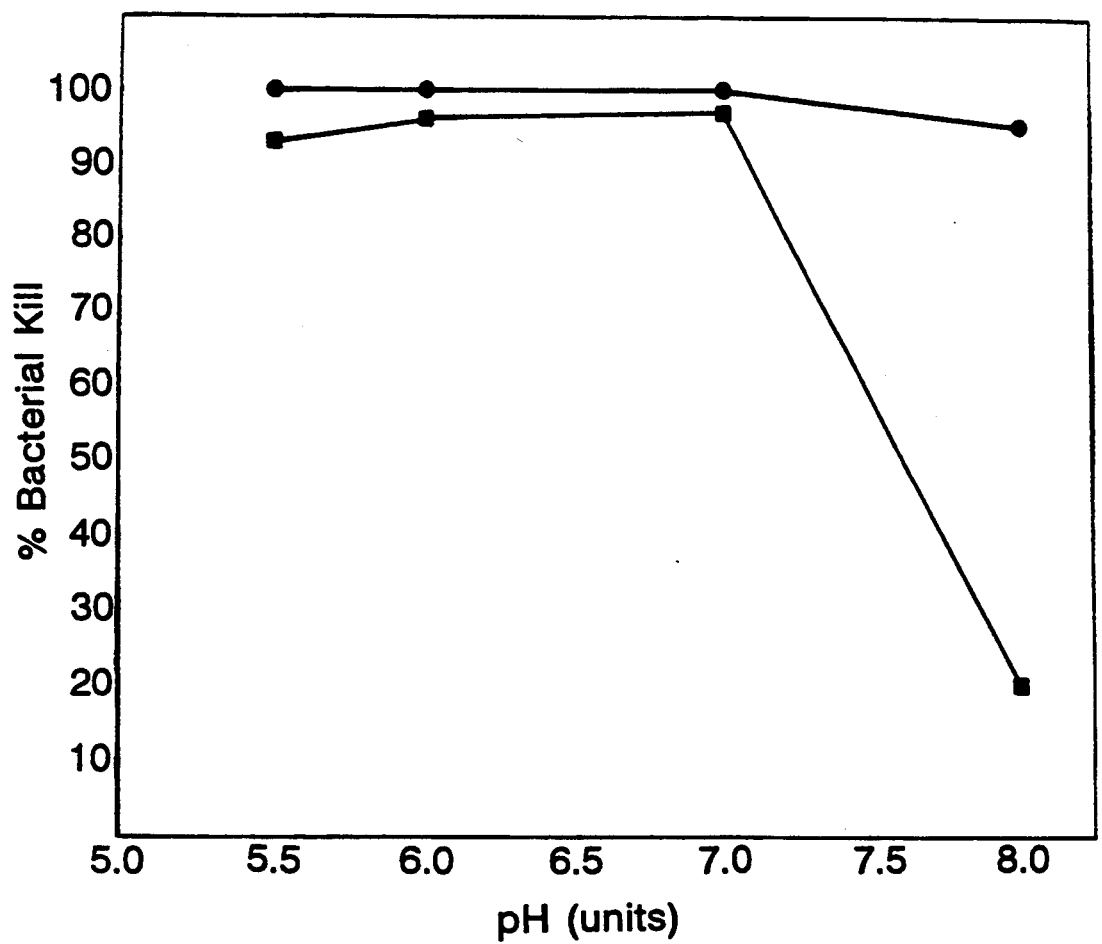

FIG. 8. Effect of pH on bactericidal activity of an HL60 derived BF

*E. coli* K12 cells ($2\times 10^5$ CFU/ml) were incubated for 30 minutes at 37° C. with 1.25 micrograms/ml (●) or 0.625 micrograms/ml (■) of HL60 crude granule extract in 50 mM citrate buffer pH 5, 5.5., and 6, and 50 mM tris-HCl, pH 7 and 8.

Figure 9:
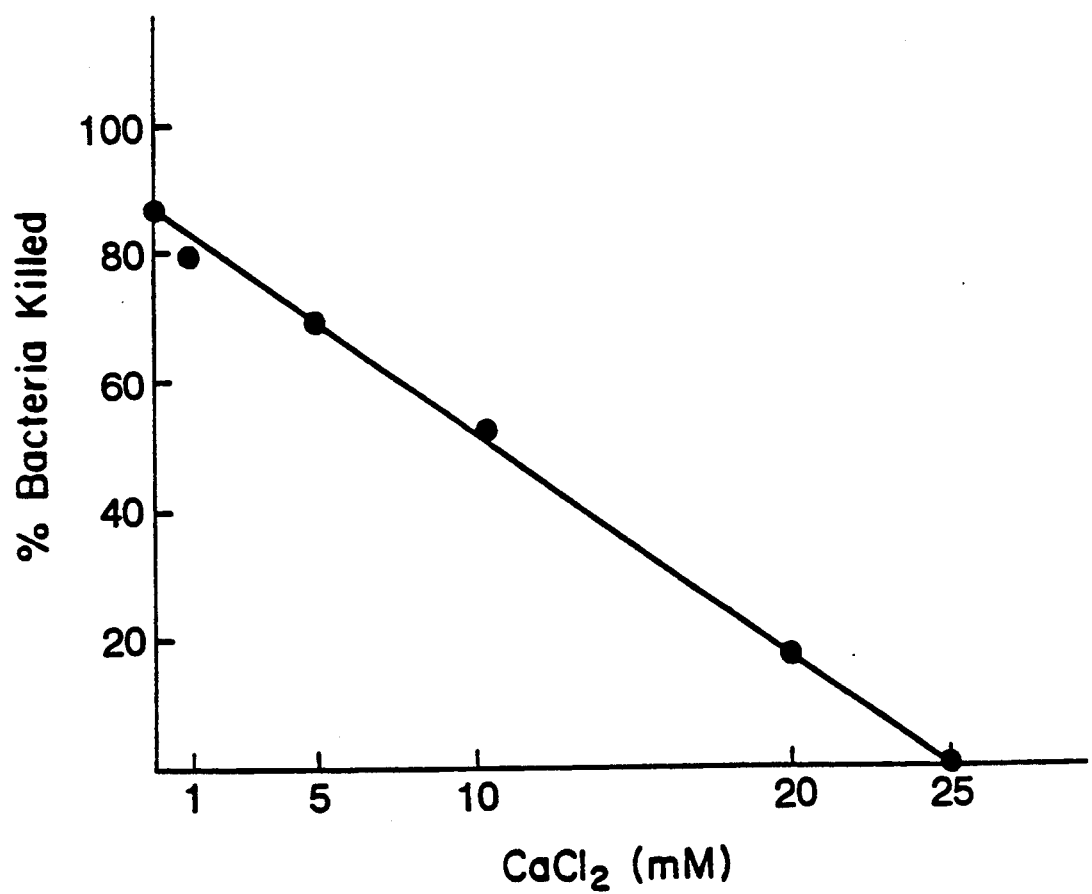

FIG. 9. Effect of $Ca^{2+}$ ions on bactericidal activity of an azurophil-derived bactericidal factor

*E. coli* K12 cells ($2.5\times 10^5$ CFU/ml) were incubated for 30 minutes at 37° C. with 2.8 micrograms/ml of azurophil granule extract in 0.05M citrate buffer 5.5, supplemented with $CaCl_2$ as shown.

Figure 10:
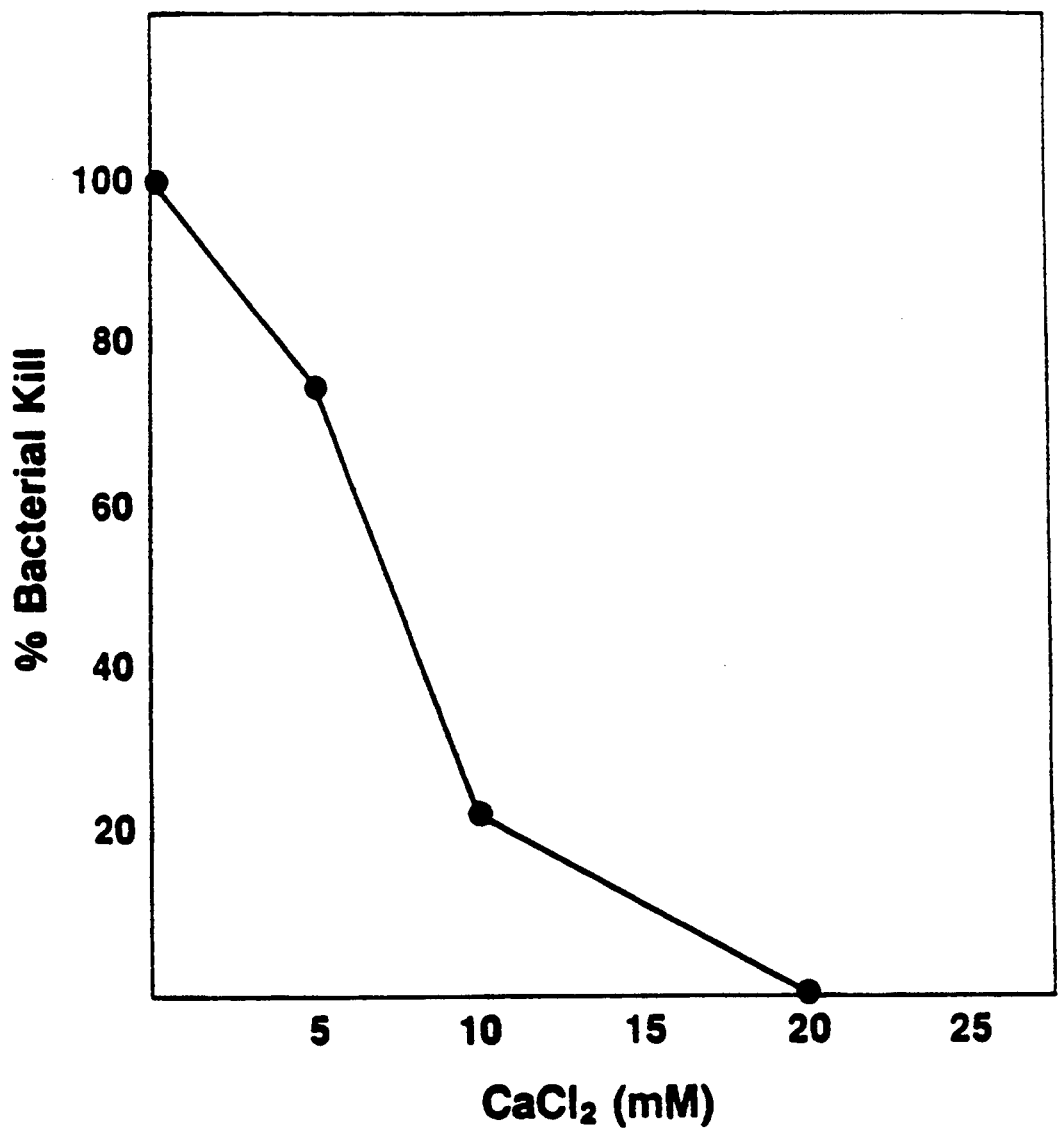

FIG. 10. Effect of $Ca^{2+}$ ions on bactericidal activity of HL60 derived BF

*E. coli* K12 cells ($2\times 10^5$ CFU/ml) were incubated for 30 minutes at 37° C. with 1.25 micrograms/ml of HL60 crude granule extract in 0.5M citrate buffer pH 5.5, supplemented with $CaCl_2$.

Figure 11:
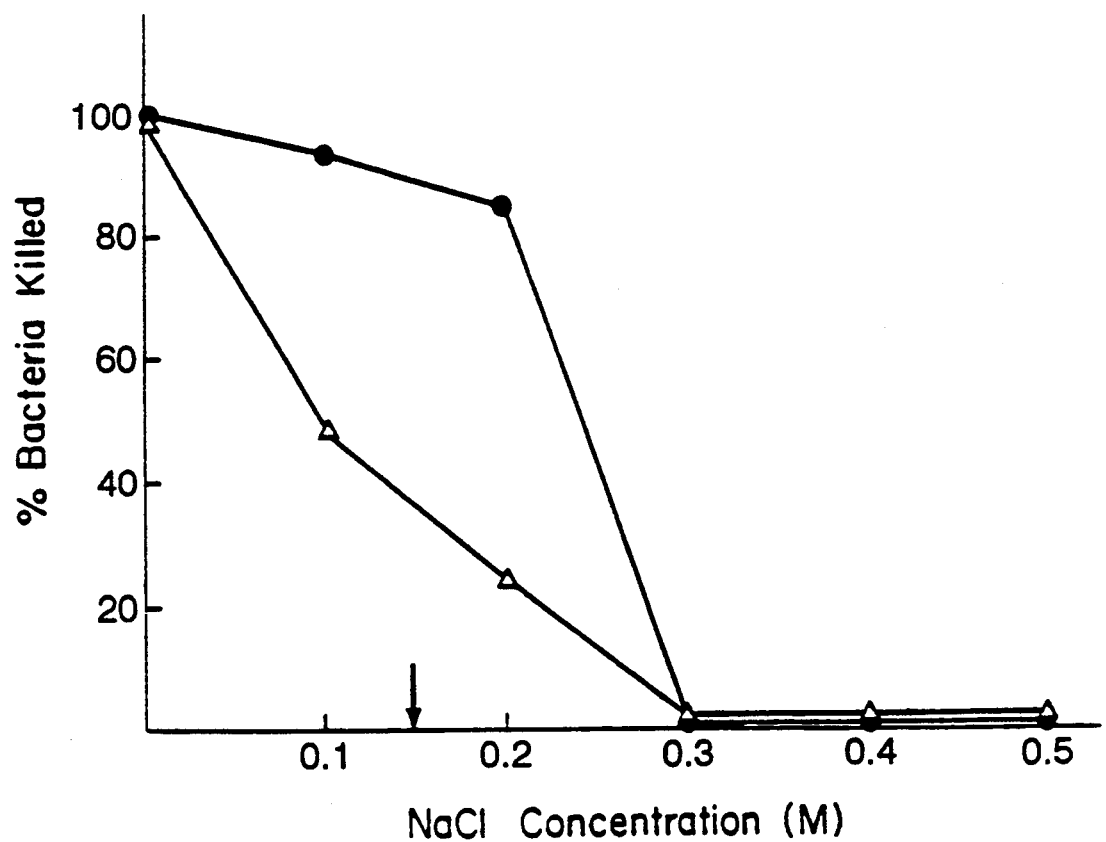

FIG. 11. Effect of sodium chloride concentration on bactericidal activity of an azurophil-derived bactericidal factor

*E. coli* K12 cells ($2.5\times 10^5$ CFU/ml) were incubated for 30 minutes at 37° C. with 2.8 micrograms/ml ( ) or 1.4 micrograms/ml (Δ) of azurophil-granule extract in 0.05M citrate buffer pH 5.5, supplemented with NaCl as shown. Arrow indicates NaCl concentration of plasma.

Figure 12:
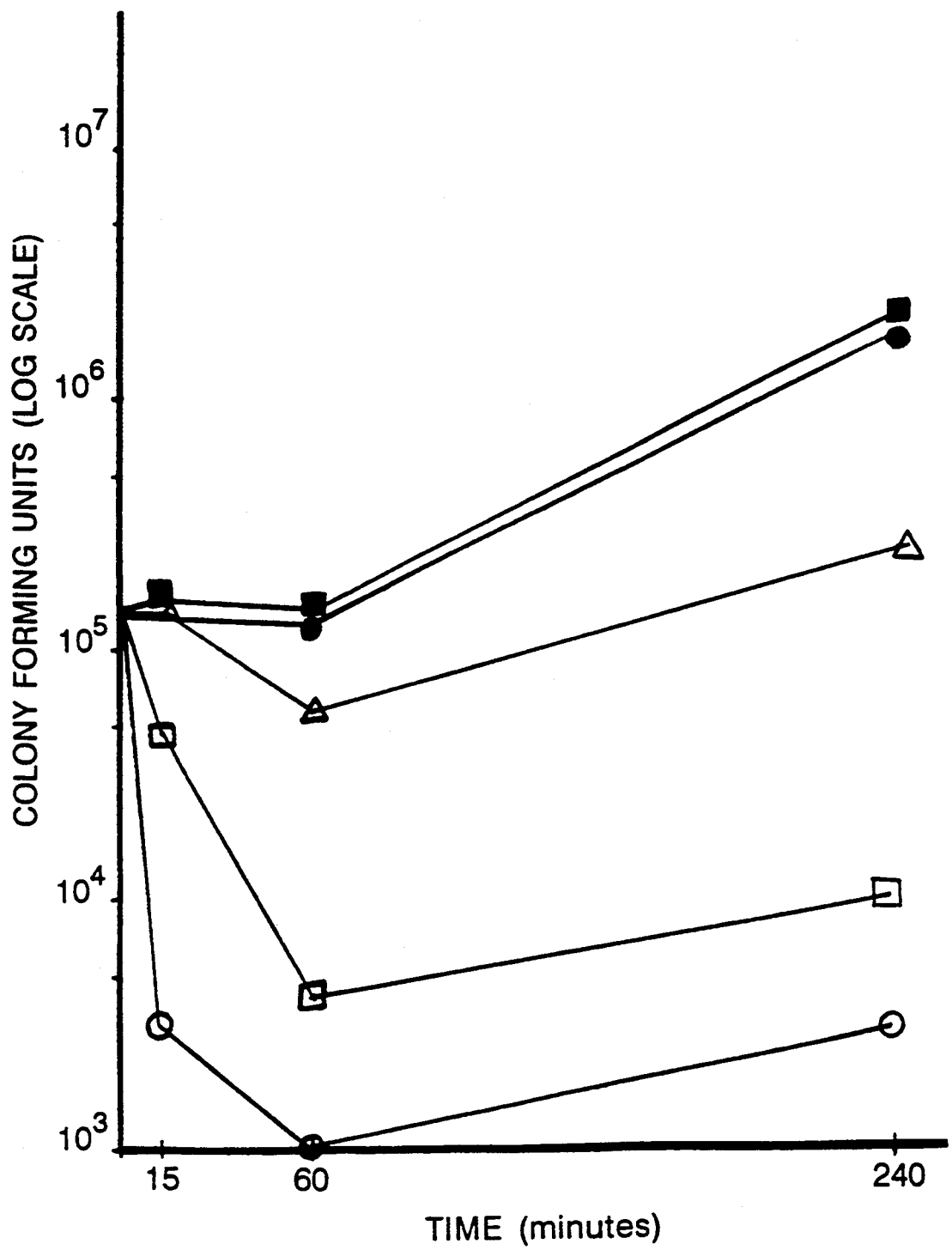
Figure 13A:
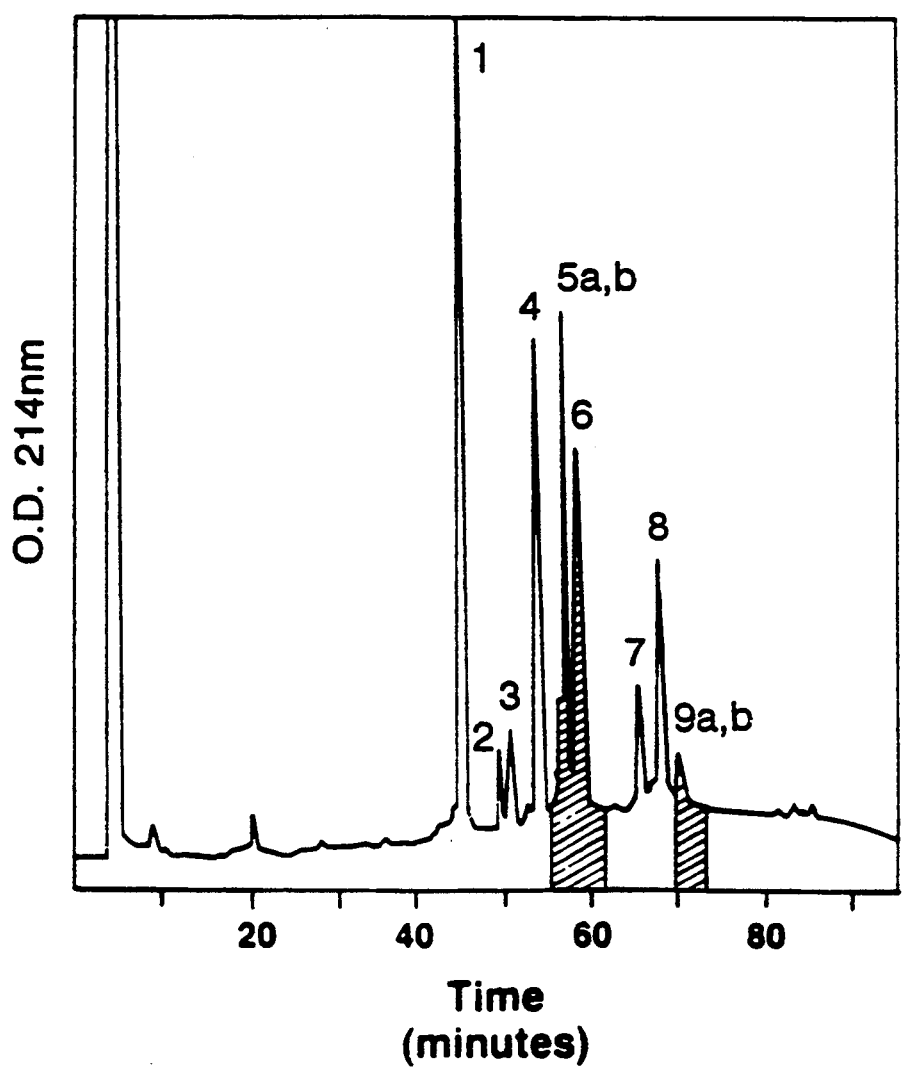
Figure 13B:
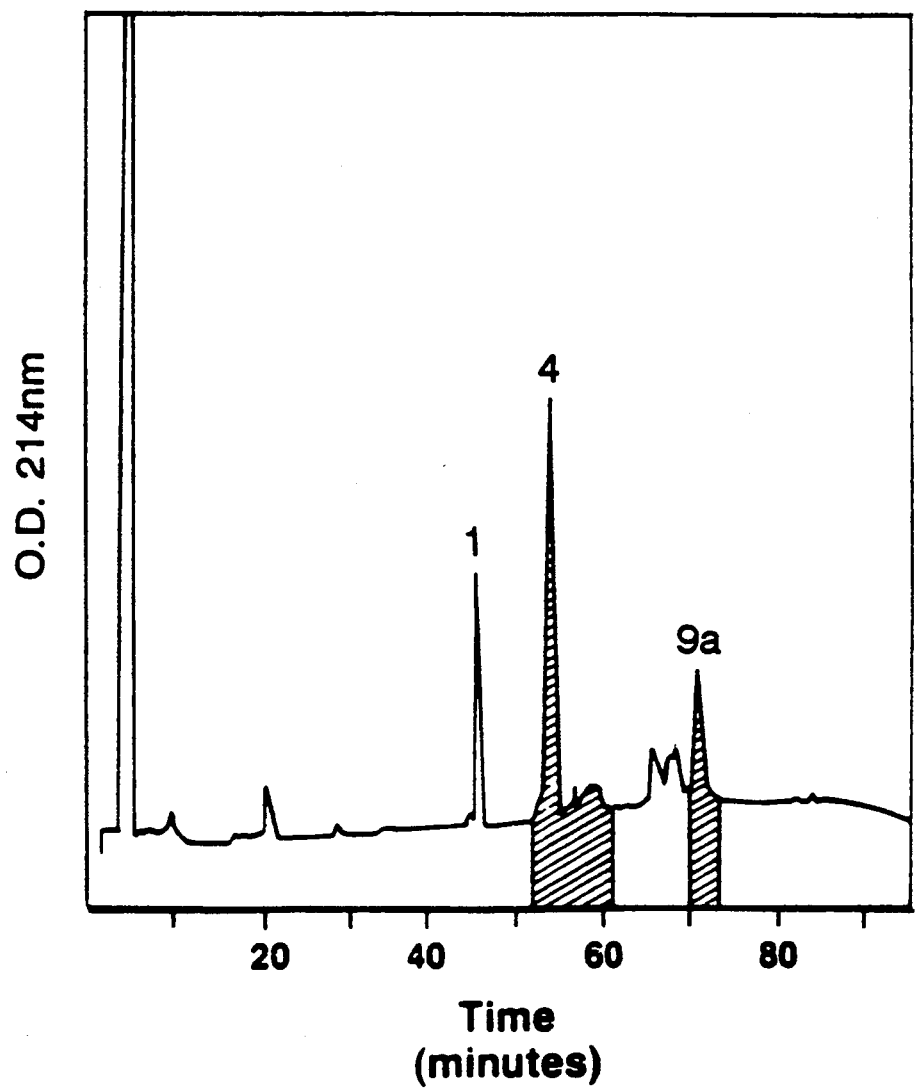
Figure 13C:
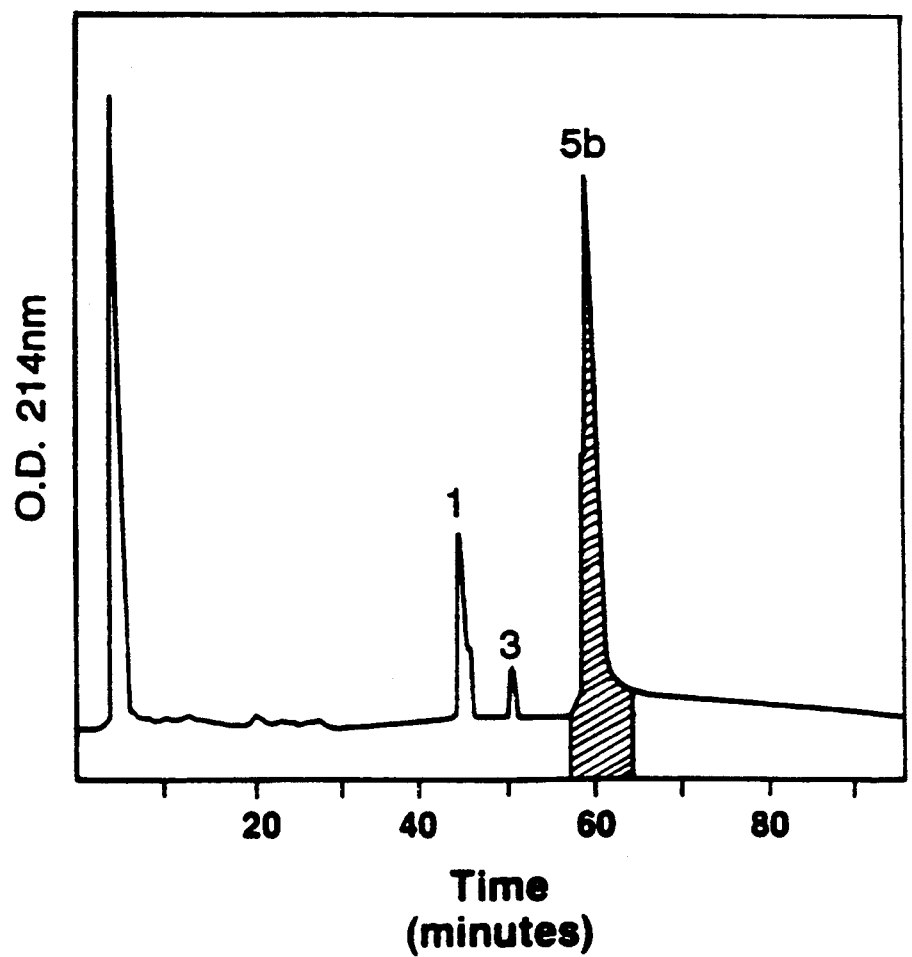

FIG. 12. Fungicidal activity of ADBF at various times and concentrations was measured:

(■) = 1.6 micrograms ADBF/ml (Δ) = 3.2 micrograms ADBF/ml (□) = 8 micrograms ADBF/ml (○) = 16 micrograms ADBF/ml (●) = control FIGS. 13A, 13B, and 13C. Reverse phase high performance liquid chromatography of ADBF Reverse phase high performance liquid chromatography was carried out as described in materials and methods. The column was monitored at 214 nm (0.5 AUFS) and 1 ml fractions collected. For assay, 100 microliters of each fraction was dried in a Savant Speed-Vac®, resuspended in 100 microliters of 0.1% acetic acid, redried and finally resuspended in 160 microliters of 0.05M citrate pH 5.5. Forty microliters of *E. coli* K12 were added to give $2\times 10^5$ CFU/ml final concentration and incubated at 37° C. for 30 minutes. The cross-hatched areas indicate regions of 100% killing. FIG. 13A represents crude ADBF, FIG. 13B, TSK purified ADBF (50–60 kD peak); and FIG. 13C TSK purified ADBF (10–20 kD peak).

FIG. 14. N-terminal sequence analysis of azurophil-derived proteins purified by reverse phase high performance liquid chromatography (single-letter designation)

Shown is the cumulative sequence data (from several analyses) corresponding to each of the major reverse phase peaks shown in FIG. 13.

Peak 1 = defensin; Peak 4 = cathepsin G;

Peak 5a = lysozyme; and Peak 8 = elastase.

Figure 15:
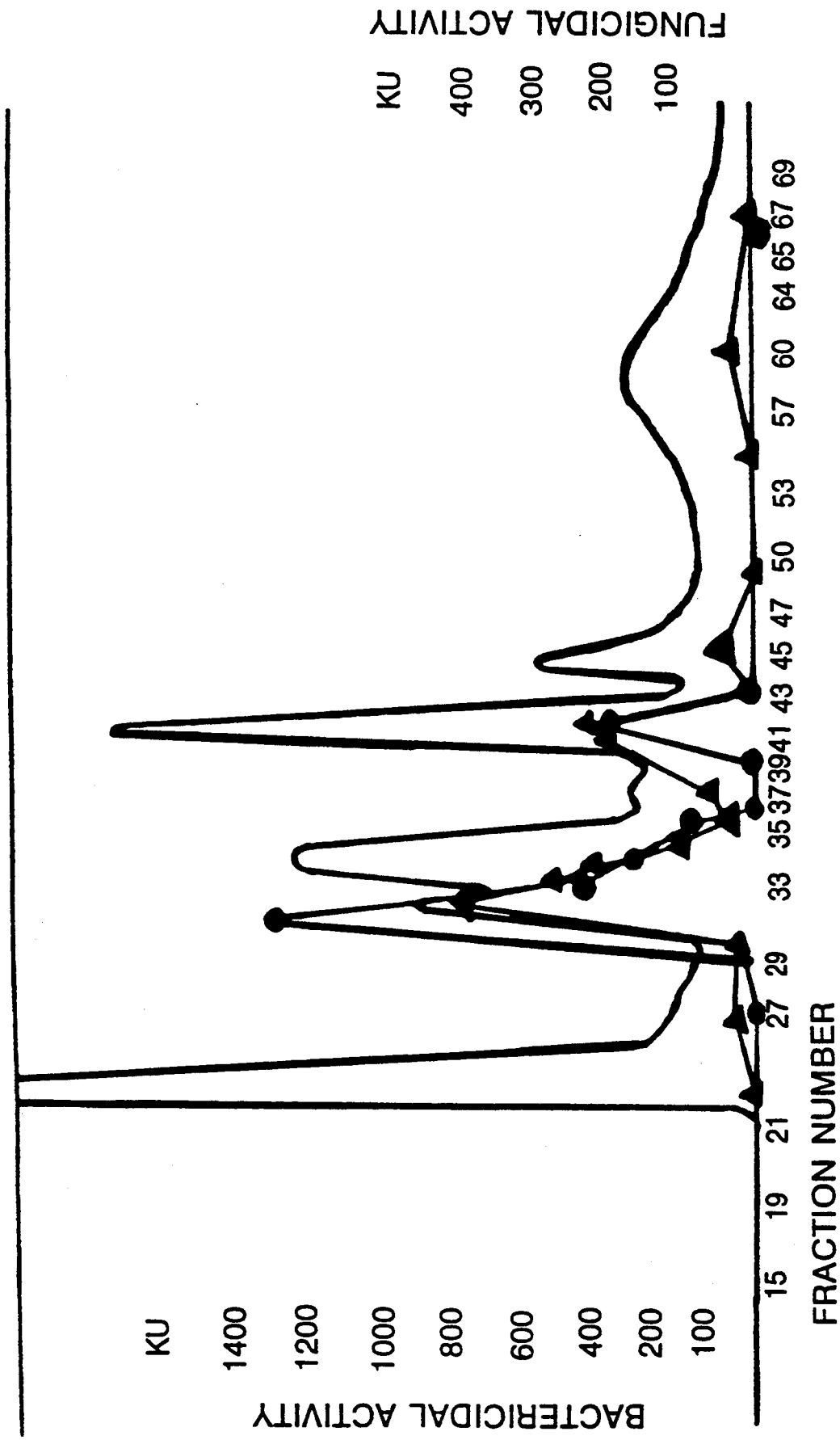

FIG. 15. ADBF size exclusion chromatogram 1 mg of ADBF was run on a TSK size exclusion column as described herein.

(●) = bactericidal activity profile.

(▲) = fungicidal activity profile.

(—) = UV profile.

Figure 16:
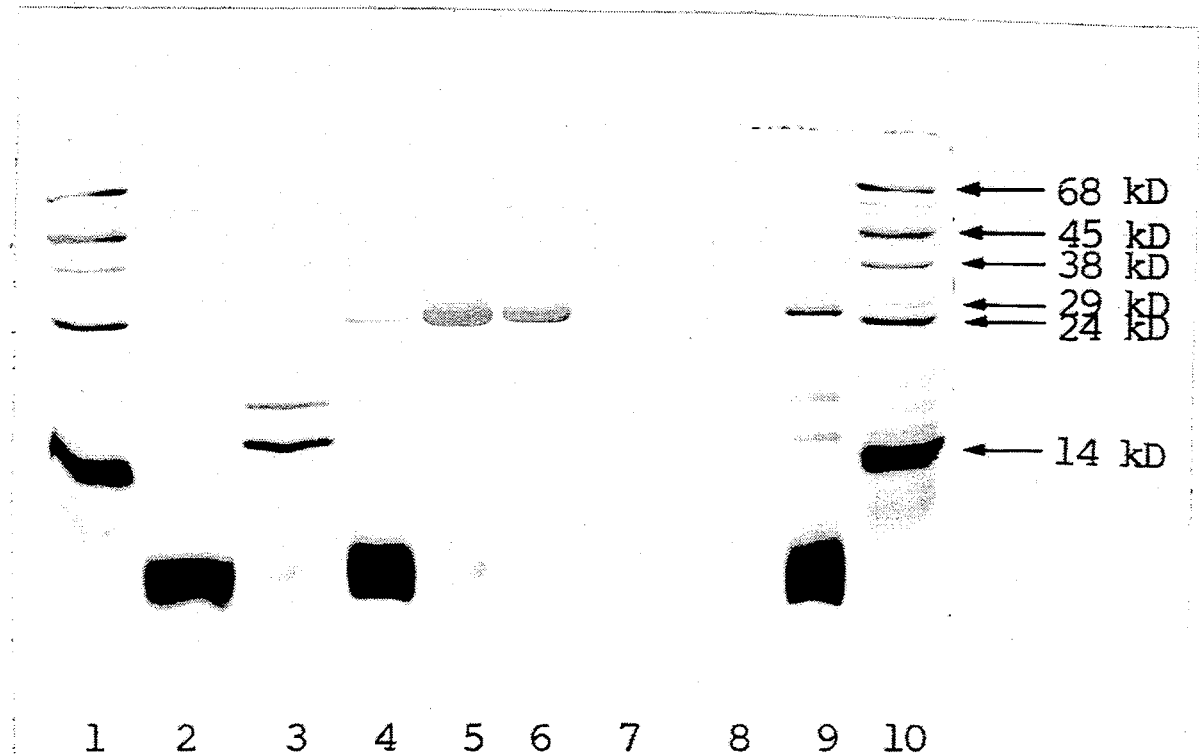

FIG. 16. SDS-PAGE of ADBF and fractions obtained from TSK size exclusion chromatograpy ADBF and various ADBF fractions from the chromatograph shown in FIG. 15 were collected and run under reducing conditions on a 15% SDS polyacrylamide gel. Lanes 1 and 10 = low molecular weight markers; lane 2 = fraction 58; lane 3 = fraction 41; lane 4 = fraction 34; lane 5 = fraction 33; lane 6 = fraction 32; lane 7 = fraction 31; lane 8 = fraction 30; and lane 9 = ADBF prior to size exclusion chromatography.

Figure 17:
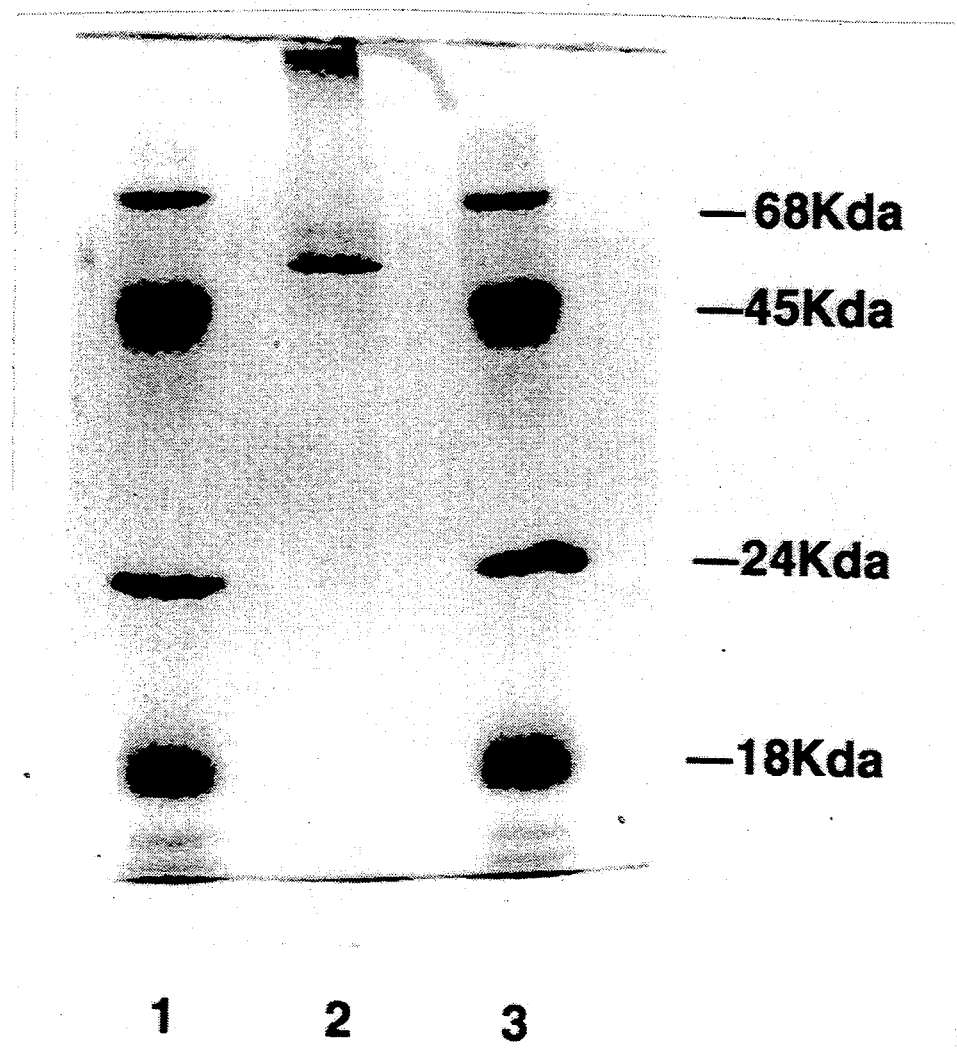

FIG. 17. SDS-PAGE of TSK—RPHPLC peak 9

Peak 9 from RPHPLC (FIG. 13) was loaded on a reducing 10% SDS polyacrylamide gel.

Lanes 1 and 3=molecular weights markers; lane 2=peak 9

Figure 18:
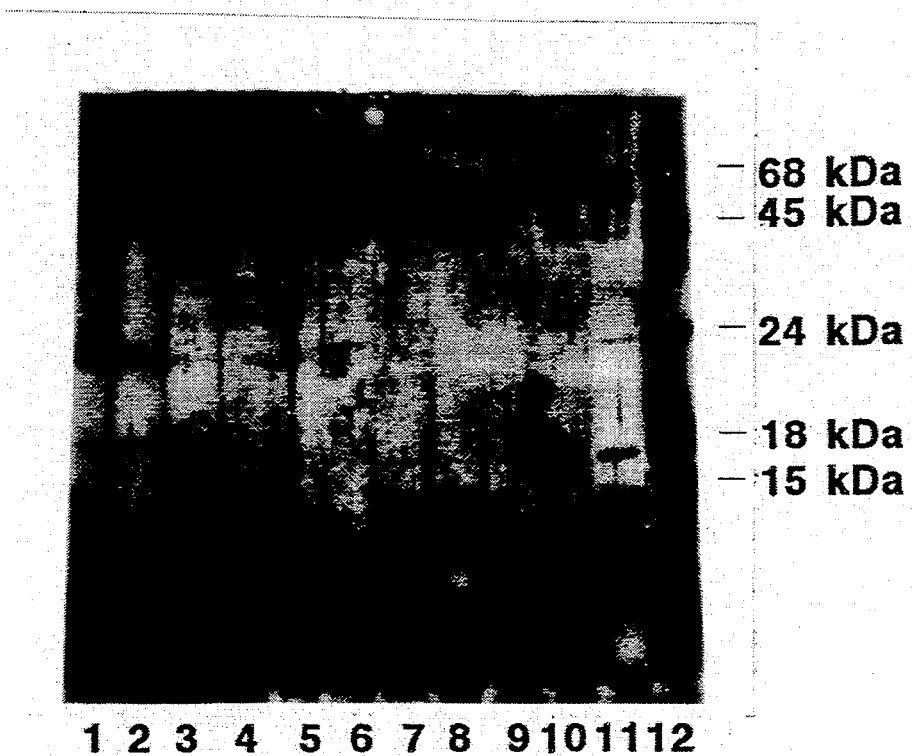

FIG. 18. SDS-PAGE of TSK-RPHPLC peak 5b

Consecutive fractions from RPHPLC corresponding to elution times from 45–65 minutes were run on a 12% SDS polyacrylamide gel.

Lane 8 contains peak 5b (from FIG. 13C) and lane 11 contains the starting material, which consisted of TSK peak fraction 42.

Figure 19:
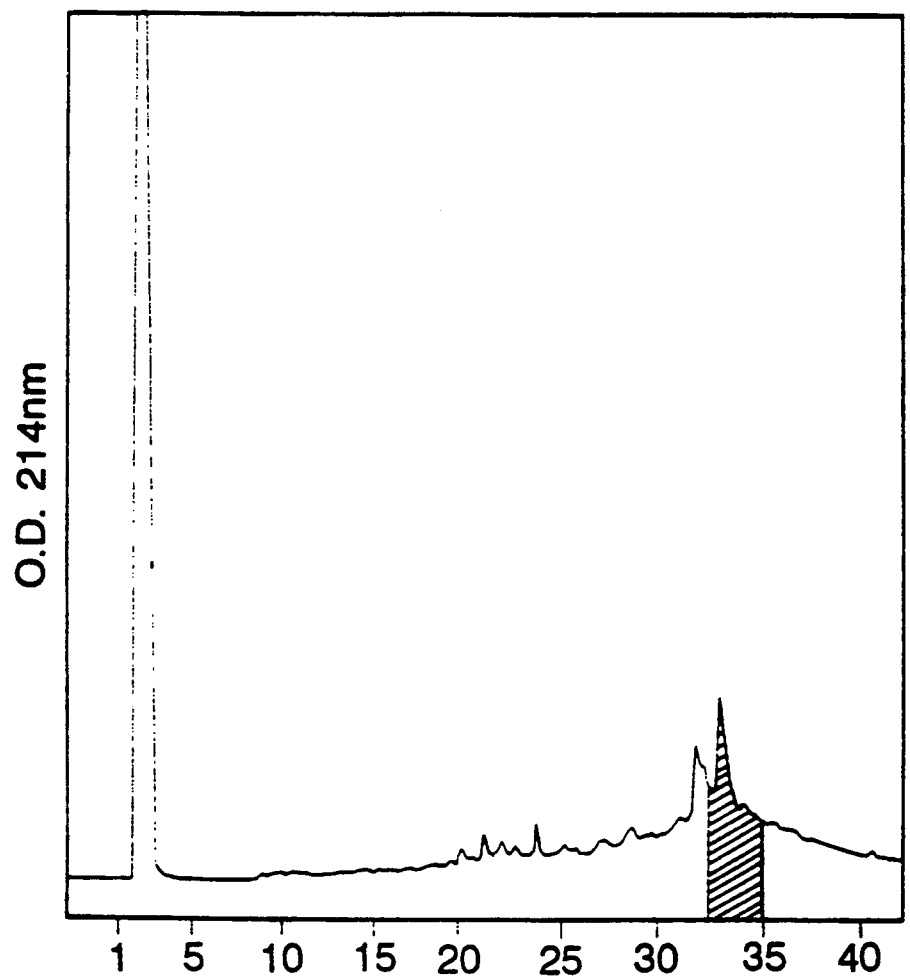

FIG. 19. RPHPLC of TSK purified HL60-derived bactericidal facet (BF)

Figure 21:
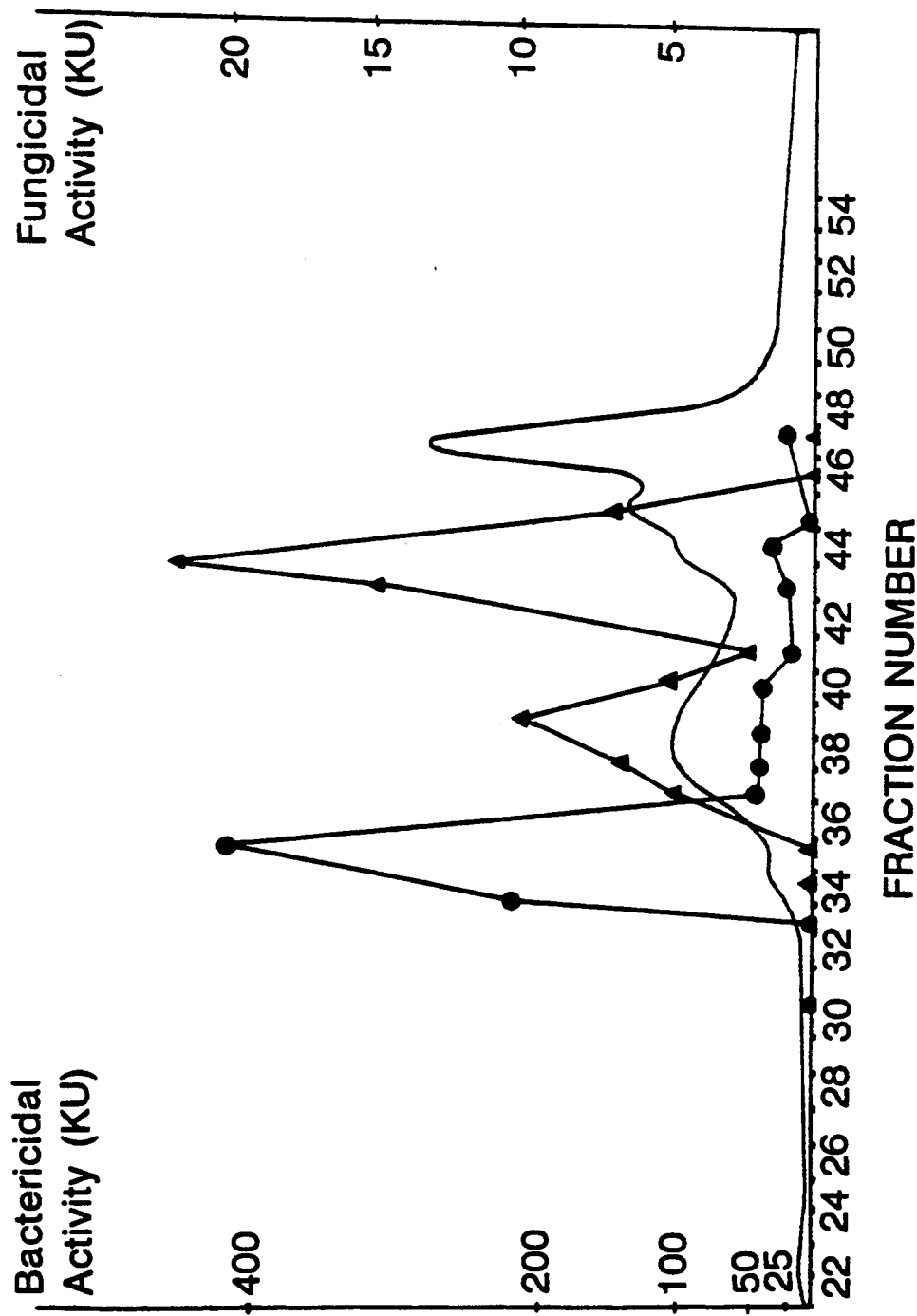

FIGS. 20A, 20B, 20C and 20D. cDNA-protein sequences of 25,000 dalton/13,000 dalton ADBF polypeptides FIG. 21. ADBF size exclusion chromatography in high salt ADBF was run on TSK size exclusion chromatography in 50 mM glycine pH 2, 500 mM NaCl.

(●)=bactericidal activity profile.
(▲)=fungicidal activity profile.
(—)=UV$_{280}$ profile.

FIG. 22. SDS-PAGE of fractions obtained from TSK size exclusion chromatography in high salt Various ADBF fractions obtained from the chromatogram shown in FIG. 21.

Lanes 1 and 3=ADBF extract; lanes 2 and 12=molecular weight markers; lanes 4 and 5=fractions 34 and 35, respectively (p54); lane 6=fraction 36; lanes 7,8, and 9=fractions 37,38, and 39, respectively (p29); lane 10=fraction 43 (p14 chiefly); lane 11=fraction 45 (p18+p14).

DETAILED DESCRIPTION OF THE INVENTION

The present invention provides a composition of matter useful as an antimicrobial agent. This composition of matter comprises at least two polypeptides selected from the group consisting of human polymorphonuclear leukocyte polypeptides having apparent molecular weights of about 3,500 daltons, about 13,000 daltons, about 18,000 daltons, about 29,000 daltons, and about 54,000 daltons. Within this application "polymorphonuclear leukocyte" means polymorphonuclear leukocyte, neutrophil, neutrophil precursor cell, and promyelocytic leukemia cell. The composition of matter has respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M.

In one embodiment of the invention, the human polymorphonuclear leukocyte polypeptides are derived from HL-60 cells. In another embodiment of the invention, the human polymorphonuclear leukocyte polypeptides are derived from KG-1 cells. In yet another embodiment of the invention the human polymorphonuclear leukocyte polypeptides are derived from azurophil granules.

In a further embodiment of the invention the polypeptide having an apparent molecular weight of about 3,500 daltons is defensin.

In another embodiment of the invention the polypeptide having an apparent molecular weight of about 13,000 comprises the 12,867 dalton polypeptide shown in FIGS. 20A and 20B from amino acid 105 to amino acid 220. In yet another embodiment of the invention any of the polypeptides having apparent molecular weights of about 18,000, about 29,000, and about 54,000 daltons may be present in an azurophil granule extract.

In one embodiment of the invention the polypeptide having an apparent molecular weight of about 18,000 daltons comprises the N-terminal amino acid sequence X-Pro-Pro-Gln-Phe-Thr-X-Ala-Gln-X-Phe-Ala-Ile-Gln-X-Ile-X-Leu-Asn-Pro.

In still another embodiment the polypeptide having an apparent molecular weight of about 29,000 daltons is elastase, cathepsin G, or a polypeptide contained in the azurophil granule extract fraction corresponding to peak 6 in FIG. 13A. In yet a further embodiment of the invention the polypeptide comprises the N-terminal amino acid sequence Ile-Val-Gly-Gly-Arg-Lys-Ala-Arg-Pro-Arg-Gln-Phe-Pro-Phe-Leu-Ala-Ser-Ile-Gln-Asn-Gln-Gly-Arg-His-Phe. Additionally the polypeptide having an apparent molecular weight of about 29,000 daltons may be contained in the azurophil granule extract fraction corresponding to peak 7 in FIG. 13A. In another embodiment of the invention the 29,000 dalton polypeptide comprises the N-terminal amino acid sequence Ile-Val-Gly-Gly-His-Glu-Ala-X-X-Pro-Ser-Asp-Pro-Tyr-Met-Asp-Ser-Leu-Asp-Met. In still a further embodiment of the invention the polypeptide having an apparent molecular weight of about 54,000 daltons comprises the N-terminal amino acid sequence Val-Asn-Pro-Gly-Val-Val-Val-Arg-Ile-Ser-Gln-Lys-Gly-Leu-Asp-Tyr-Ala-Ser-Gln-Gln-Gly-Thr-Ala-Ala-Leu-Gln-X-X-Leu-Lys-His-Ile-Lys-Ile-Pro-Asp-Tyr-Leu.

The composition of matter of this invention may be used as a preservative, a disinfectant, or as a therapeutic agent. Bacteria against which the composition of matter has bactericidal activity include Gram positive and Gram negative bacteria. Example of such Gram positive bacteria are Staphylococcus aureus, β-hemolytic Streptococci, e.g., Streptococcus pneumonias, and Listeria. Examples of such Gram negative bacteria are Pseudomonas aeruginosa, Escherichia coli, and Salmonella typhimurium. Additionally, fungi against which the composition of matter acts as an antimicrobial agent include yeast. In one embodiment of the invention, the yeast is Candida albicans.

The composition of matter provided by the present invention retains greater than 80% of its oxygen-independent, antimicrobial activity upon storage for seven days at about pH 2.0 and about at 4° C.

A method for killing bacteria or fungi is also provided. This method comprises contacting the bacteria or fungi with an effective bacterial or fungal killing amount of a composition of matter provided by the present invention, typically dissolved in an appropriate buffer. Examples of appropriate buffers are known in the art and include phosphate buffer or phosphate buffered saline at physiologic pH.

A pharmaceutical composition useful for treating bacterial or fungal infections is further provided by the present invention. This pharmaceutical composition comprises an effective bacterial or fungal killing amount of the composition of matter of the present invention and a pharmaceutically acceptable carrier. Pharmaceutically acceptable carriers are known in the art and are disclosed in The Pharmacopeia of the United States and the National Formulary.

Depending on the specific application contemplated, the pharmaceutical composition provided by the subject invention may be formulated as a solution, suspension, parental preparation, ointment, cream, lotion, spray, powder, tablet or capsule. Parental preparations may include a vehicle such as specially distilled, pyrogen-free water, phosphate buffer, or normal saline. Ointments, creams, lotions and sprays may include a carrier such as vegetable or mineral oil, white petrolatum, or a high molecular weight alcohol, i.e., greater than C12. Tablets or capsules may include diluents, e.g., lactose, binders, lubricants, e.g., stearic acid, and a disintegrator, e.g., corn starch.

Also provided is a method for treating a subject having a bacterial or fungal infection which comprises administering to the subject an effective bacterial or fungal killing amount of the pharmaceutical composition of the present invention.

The invention further provides a method for preparing a composition of matter useful as an antimicrobial agent. This method comprises substantially separating polymorphonuclear leukocytes from blood so as to obtain a polymorphonuclear leukocyte-enriched preparation. This preparation is suspended in a suitable buffer, e.g., phosphate buffer, the resulting suspension is treated with a suitable protease inhibitor, e.g., diisopropylfluorophosphate, and the suspended cells are treated under lysing conditions so as to obtain a suspension of lysed leukocytes. The suspension of lysed leukocytes is treated with a suitable chelating agent, e.g., EDTA or the calcium chelator EGTA, and the treated suspension then centrifuged so as to obtain a nuclei/unbroken cell phase and a postnuclear supernatant. The postnuclear supernatant is recovered and fractionated on a density gradient and the fraction which includes azurophil granules is collected and suspended in a buffer which has a pH of about 7.0, e.g., the relaxation buffer described herein. The resulting azurophil granule suspension is treated with a reagent having a pH less than about 8.0 and capable of solubilizing azurophil membrane proteins. The treated suspension is separated into a solid phase and a supernatant and the supernatant is then recovered, and thereby the composition of matter useful as an antimicrobial agent obtained.

In one embodiment of the invention, the suitable protease inhibitor is diisopropylfluorophosphate. In another embodiment of the invention, the blood sample is obtained from a human. In yet a further embodiment of the invention, the polymorphonuclear leukocyte enriched preparation comprises greater than about 95% polymorphonuclear leukocytes and less than about 3% eosinophils. In still another embodiment of the invention, the polymorphonuclear leukocyte suspension is treated by nitrogen cavitation to obtain a lysed leukocyte suspension.

In a further embodiment of the invention, the density gradient used to fractionate the postnuclear supernatant comprises a discontinuous Percoll density gradient. In still another embodiment of the invention, the fractionating material is separated from the azurophil granules prior to suspending the collected azurophil granules in a neutral buffer.

In yet a further embodiment of the invention, the azurophil granule suspension may be treated so as to lyse the azurophil granules, and the resulting membrane fragments are recovered. These recovered membrane fragments are then treated with an extracting reagent so as to obtain an extracting reagent/azurophil membrane suspension. In one embodiment of the invention, the extracting reagent has a pH of less than about 4.0. In another embodiment of the invention, the extracting reagent has a pH of about 2.0. In still a further embodiment of the invention, the extracting reagent is a nonionic detergent having a pH of about 7.0.

The present invention also provides a purified polypeptide useful as an antimicrobial agent. This polypeptide comprises a human polymorphonuclear leukocyte polypeptide having a predicted molecular weight of 24,823 daltons and the amino acid sequence shown in FIGS. 20A and 20B, or a fragment derived therefrom. A DNA molecule encoding this polypeptide is also provided which comprises the nucleotide sequence shown in FIGS. 20A and 20B.

Within the context of the present invention, it is understood that variations in proteins and nucleic acids exist among individuals, e.g. amino acid or nucleotide substitutions, deletions, insertions, and degree or location of glycosylation, and that functional derivatives resulting therefrom are included within the scope of the present invention.

In one embodiment of the invention the purified polypeptide has an apparent molecular weight of about 13,000 daltons. In a preferred embodiment of the invention the polypeptide has a predicted molecular weight of 12,867 daltons. This polypeptide may comprise the amino acid sequence shown in FIGS. 20A and 20B from amino acid 105 to amino acid 220. A DNA molecule encoding this polypeptide is provided. In one embodiment, the DNA molecule comprises the DNA molecule comprises the DNA sequence shown in FIGS. 20A and 20B from nucleotide 369 to nucleotide 716. In still another embodiment of the invention, the polypeptide has an apparent molecular weight of about 18,000 daltons. A DNA molecule encoding this polypeptide is further provided.

A method for killing a microorganism, e.g. a bacteria, fungus, or virus, is also provided. This method comprises contacting the microorganism with an effective microorganism killing amount of the polypeptide having a predicted molecular weight of 24,823 daltons, or a fragment thereof, provided by the present invention.

A vector which comprises the DNA molecule encoding the polypeptide of the present invention having a predicted molecular weight of 24,823 daltons, or a fragment thereof, is also provided. In one embodiment of the invention the vector comprises a plasmid. Moreover, a host vector system for the production of the 24,823 dalton polypeptide, or a fragment thereof, is provided which comprises a plasmid of the present invention in a suitable host. This host vector system may be grown under suitable conditions which permit the production of the 24,823 dalton polypeptide of the present invention, or a fragment thereof, and the resulting polypeptide may be recovered.

A method is also provided for preparing the purified 24,823 dalton polypeptide, or fragment thereof, which comprises culturing neutrophil precursor cells, harvesting the cells and suspending them in a suitable buffer. The resulting neutrophil precursor cell suspension is treated so as to obtain a suspension of lysed neutrophil precursor cells, and the suspension is separated so as to obtain a nuclei and unbroken cell phase and a post nuclear supernatant. The postnuclear supernatant is recovered and treated with an extracting reagent having a pH less than about 8.0 and capable of solubilizing membrane proteins so as to obtain an extracting reagent phase and an insoluble membrane phase. The extracting reagent phase is separated from the insoluble membrane phase so as to obtain a soluble protein phase and an insoluble membrane phase. The soluble protein phase is recovered and purified so as to obtain the 24,823 dalton polypeptide of the present invention, or fragment thereof.

In one embodiment of the invention, the neutrophil precursor cells are HL60 cells. In another embodiment of the invention, prior to treating the neutrophil precursor cell suspension so as to obtain a suspension of lysed neutrophils, the suspension is treated with a suitable protease inhibitor. In another embodiment of the invention, prior to separating the suspension of lysed neutorphils, the suspension is treated with a suitable chelating agent.

In yet another embodiment of the invention, the soluble protein phase is purified by ion exchange chromatography. Moreover, the soluble protein phase may be purified by size exclusion chromatography, affinity chromatography or immuno-affinity chromatography.

The present invention also provides a pharmaceutical composition which comprises the 24,823 dalton polypeptide, or fragment thereof, provided herein and a pharmaceutically acceptable carrier. This pharmaceutical composition may be used to treat a subject having a bacterial or fungal infection by administering to the subject an effective bacterial or fungal killing amount of the pharmaceutical composition.

The present invention further provides another purified polypeptide useful as an antimicrobial agent. This polypeptide comprises a human polymorphonuclear leukocyte polypeptide having an apparent molecular weight of about 18,000 daltons. In one embodiment of the invention the polypeptide has respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M. In another embodiment of the invention the polypeptide comprises the N-terminal amino acid sequence X-Pro-Pro-Gln-Phe-Thr-X-Ala-Gln-X-Phe-Ala-Ile-Gln-X-Ile-X-Leu-Asn-Pro.

A method for killing a microorganism is also provided. This method comprises contacting the microorganism with an effective microorganism killing amount of the 18,000 dalton polypeptide of the present invention.

Further provided is a DNA molecule which encodes the 18,000 dalton polypeptide of the present invention. A vector which comprises the DNA molecule of the present invention is also provided. In one embodiment of the invention the vector comprises a plasmid. Moreover, a host vector system for the production of the 18,000 dalton polypeptide of the present invention is provided which comprises a plasmid of the present invention in a suitable host. This host vector system may be grown under suitable conditions which permit the production of the 18,000 dalton polypeptide of the present invention and the resulting polypeptide may be recovered.

A method is also provided for preparing the purified 18,000 dalton polypeptide of the present invention which comprises culturing neutrophil precursor cells, harvesting the cells and suspending them in a suitable buffer. The resulting neutrophil precursor cell suspension is treated so as to obtain a suspension of lysed neutrophil precursor cells, and the suspension is separated so as to obtain a nuclei and unbroken cell phase and a post nuclear supernatant. The postnuclear supernatant is recovered and treated with an extracting reagent having a pH less than about 8.0 and capable of solubilizing membrane proteins so as to obtain an extracting reagent phase and an insoluble membrane phase. The extracting reagent phase is separated from the insoluble membrane phase so as to obtain a soluble protein phase and an insoluble membrane phase. The soluble protein phase is recovered and purified so as to obtain a 18,000 dalton polypeptide.

In one embodiment of the invention, the neutrophil precursor cells are HL60 cells. In another embodiment of the invention, prior to treating the neutrophil precursor cell suspension so as to obtain a suspension of lysed neutrophils, the suspension is treated with a suitable protease inhibitor. In another embodiment of the invention, prior to separating the suspension of lysed neutorphils, the suspension is treated with a suitable chelating agent.

In yet another embodiment of the invention, the soluble protein phase is purified by ion exchange chromatography. Moreover, the soluble protein phase may be purified by size exclusion chromatography, affinity chromatography or immuno-affinity chromatography.

The present invention also provides a pharmaceutical composition which comprises the 18,000 dalton polypeptide provided herein and a pharmaceutically acceptable carrier. This pharmaceutical composition may be used to treat a subject having a microorganism infection by administering to the subject an effective microorganism killing amount of the pharmaceutical composition.

The present invention further provides yet another a purified polypeptide useful as an antimicrobial agent which comprises a human polymorphonuclear leukocyte polypeptide having an apparent molecular weight of about 54,000 daltons. This polypeptide has respiratory burst-independent, antibacterial activity at a pH from about 5.0 to about 8.0, at calcium ion concentrations up to about 10 mM, and at sodium chloride concentrations up to about 0.3M. In one embodiment of the invention the polypeptide additionally has antifungal activity at a pH from about 5.0 to about 8.0, at calcium ion concentrations up to about 10 mM, and at sodium chloride concentrations up to about 0.15M.

In another embodiment of the invention, the polypeptide comprises the N-terminal amino acid sequence Val-Asn-Pro-Gly-Val-Val-Val-Arg-Ile-Ser-Gln-Lys-Gly-Leu-Asp-Tyr-Ala-Ser-Gln-Gln-Gly-Thr-Ala-Ala-Leu-Gln-X-X-Leu-Lys-His-Ile-Lys-Ile-Pro-Asp-Tyr-Leu.

A method for killing bacteria or fungi is also provided. This method comprises contacting the bacteria or fungi with an effective bacterial or fungal killing amount of the 54,000 dalton polypeptide of the present invention.

Further provided is a DNA molecule which encodes the 54,000 dalton polypeptide of the present invention and a vector which comprises the DNA molecule The present invention also provides a vector which comprises the plasmid of the present invention. Moreover, a host vector system for the production of the 54,000 dalton polypeptide of the present invention is provided which comprises a plasmid of the present invention in a suitable host. This host vector system may be grown under suitable conditions which permit the production of the 54,000 polypeptide of the present invention and the resulting polypeptide may be recovered.

A method is also provided for preparing the purified 54,000 dalton polypeptide of the present invention which comprises culturing neutrophil precursor cells, harvesting the cells and suspending them in a suitable buffer. The resulting neutrophil precursor cell suspension is treated so as to obtain a suspension of lysed neutrophil precursor cells and the suspension is separated so as to obtain a nuclei and unbroken cell phase and a postnuclear supernatant. The postnuclear supernatant is recovered and treated with an extracting reagent having a pH less than about 8.0 and capable of solubilizing membrane proteins so as to obtain an extracting reagent phase and an insoluble membrane phase. The extracting reagent phase is separated from the insoluble membrane phase so as to obtain a soluble protein phase and an insoluble membrane phase. The soluble protein phase is then recovered and purified so as to obtain a 54,000 dalton polypeptide.

In one embodiment of the invention, the neutrophil precursor cells are HL60 cells. In another embodiment of the invention, prior to treating the neutrophil precursor cell suspension so as to obtain a suspension of lysed neutrophils, the suspension is treated with a suitable protease inhibitor. In another embodiment of the invention, prior to separating the suspension of lysed neutorphils, the suspension is treated with a suitable chelating agent.

In yet another embodiment of the invention, the soluble protein phase is purified by ion exchange chromatography. Moreover, the soluble protein phase may be purified by size exclusion chromatography, affinity chromatography or immuno-affinity chromatography.

The present invention also provides a pharmaceutical composition which comprises the 54,000 dalton polypeptide provided herein and a pharmaceutically acceptable carrier. This pharmaceutical composition may be used to treat a subject having a bacterial infection by administering to the subject an effective bacterial killing amount of the pharmaceutical composition. In another embodiment of the invention the pharmaceutical composition may be used to treat a subject having a bacterial or fungal infection by administering to the subject an effective bacterial or fungal killing amount of the pharmaceutical composition.

The present invention further provides another purified polypeptide useful as an antimicrobial agent. This polypeptide comprises a human polymorphonuclear leukocyte polypeptide having an apparent molecular weight of about 29,000 daltons. This polypeptide additionally has respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M.

In one embodiment of the invention the polypeptide is derived from the azurophil granule extract fraction corresponding to peak 6 in FIG. 13A. In another embodiment the purified polypeptide which comprises the N-terminal amino acid sequence Ile-Val-Gly-Gly-Arg-Lys-Ala-Arg-Pro-Arg-Gln-Phe-Pro-Phe-Leu-Ala-Ser-Ile-Gln-Asn-Gln-Gly-Arg-His-Phe. In still another embodiment of the invention the polypeptide is derived from the azurophil granule extract fraction corresponding to peak 7 in FIG. 13A. In yet a further embodiment the purified polypeptide comprises the N-terminal amino acid sequence Ile-Val-Gly-Gly-His-Glu-Ala-X-X-Pro-Ser-Asp-Pro-Tyr-Met-Asp-Ser-Leu-Asp-Met.

A method for killing bacteria or fungi is also provided. This method comprises contacting the bacteria or fungi with an effective bacterial or fungal killing amount of the 29,000 dalton polypeptide of the present invention.

Further provided is a DNA molecule which encodes the 29,000 dalton polypeptide of the present invention. A vector which comprises the DNA molecule of the present invention is also provided. In one embodiment of the invention the vector comprises a plasmid. Moreover, a host vector system for the production of the 29,000 dalton polypeptide of the present invention is provided which comprises a plasmid of the present invention in a suitable host. This host vector system may be grown under suitable conditions which permit the production of the 29,000 dalton polypeptide of the present invention and the resulting polypeptide may be recovered.

A method is also provided for preparing the purified 29,000 dalton polypeptide of the present invention which comprises culturing neutrophil precursor cells, harvesting the cells and suspending them in a suitable buffer. The resulting neutrophil precursor cell suspension is treated so as to obtain a suspension of lysed neutrophil precursor cells, and the suspension is separated so as to obtain a nuclei and unbroken cell phase and a post nuclear supernatant. The postnuclear supernatant is recovered and treated with an extracting reagent having a pH less than about 8.0 and capable of solubilizing membrane proteins so as to obtain an extracting reagent phase and an insoluble membrane phase. The extracting reagent phase is separated from the insoluble membrane phase so as to obtain a soluble protein phase and an insoluble membrane phase. The soluble protein phase is recovered and purified so as to obtain a 29,000 dalton polypeptide.

In one embodiment of the invention, the neutrophil precursor cells are HL60 cells. In another embodiment of the invention, prior to treating the neutrophil precursor cell suspension so as to obtain a suspension of lysed neutrophils, the suspension is treated with a suitable protease inhibitor. In another embodiment of the invention, prior to separating the suspension of lysed neutorphils, the suspension is treated with a suitable chelating agent.

In yet another embodiment of the invention, the soluble protein phase is purified by ion exchange chromatography. Moreover, the soluble protein phase may be purified by size exclusion chromatography, affinity chromatography or immuno-affinity chromatography.

The present invention also provides a pharmaceutical composition which comprises the 29,000 dalton polypeptide provided herein and a pharmaceutically acceptable carrier. This pharmaceutical composition may be used to treat a subject having a bacterial or fungal infection by administering to the subject an effective bacterial or fungal killing amount of the pharmaceutical composition.

A method for killing fungi is also provided which comprises contacting the fungi with an effective fungal killing amount of elastase. Another method for killing fungi is provided which comprises contacting the fungi with an effective fungal killing amount of cathepsin G.

The present invention also provides a pharmaceutical composition which comprises elastase and a pharmaceutically acceptable carrier. This pharmaceutical composition may be used in a method for treating a subject having a fungal infection by administering to the subject an effective fungal killing amount of the pharmaceutical composition.

Yet another pharmaceutical composition is provided which comprises cathepsin G and a pharmaceutically acceptable carrier. This pharmaceutical compostion is useful in a method for treating a subject having a fungal infection by administering to the subject an effective fungal killing amount of the pharmaceutical composition.

A purified polypeptide useful as an antimicrobial agent which comprises a human polymorphonuclear leukocyte polypeptide having an apparent molecular weight of about 25,000 daltons, respiratory burst-independent, antimicrobial activity against bacteria and fungi at a pH from about 5.0 to about 8.0 and at calcium ion concentrations up to about 10 mM, bacteriocidal activity at sodium chloride concentrations up to about 0.3M, and fungicidal activity at sodium chloride concentrations up to about 0.15M The compositions of matter, polypeptides, and methods of the present invention will be better understood by reference to the following experiments and examples, which are provided for purposes of illustration and are not to be construed as in any way limiting the scope of the invention, which is defined by the claims appended.

Materials and Methods

Isolation of Neutrophils

Blood obtained from healthy donors was anticoagulated with 25 mM sodium citrate and mixed with an equal volume of 6% dextran in 0.9% NaCl to enhance the sedimentation of erythrocytes. After 60 minutes at room temperature, the leukocyte-rich supernatant was collected and centrifuged at 200× g for 10 minutes. The cell pellets were resuspended in 0.9% NaCl and PMNs were separated from mononuclear cells by centrifugation through Ficoll-Hypaque. Contaminating erythrocytes were removed by two successive cycles of hypotonic lysis as described (8, 9). More than 98% of the cells were PMNs, of which more than 95% were neutrophils and less than 3% were eosinophils. This preparation was referred to as neutrophils. One unit of blood yielded 109 neutrophils.

Subcellular Fractionation of Neutrophils

Isolated neutrophils in phosphate-buffered saline ($2\times10^7$ cells/ml) were treated with 5 mM diisopropylfluorophosphate (DFP) for 15 minutes at 4° C. The DFP-treated cells were centrifuged at 130× g for 10 minutes at 4° C., and the resulting pellet was resuspended in an ice-cold buffer containing 100 mM KCl, 3 mM NaCl, 1 mM $ATP(Na)_2$, 3.5 mM $MgCl_2$, and 10 mM Pipes, pH 7.3 (relaxation buffer). The cell suspension was disrupted by nitrogen cavitation for 20 minutes at 350 psi in a bomb (Parr Instrument Company, Moline, Ill.) at 4° C. and the cavitate was collected into the $Ca^{2+}$ ion chelator EGTA, pH 7.4, at a final concentration of 1.5 mM. Nuclei and unbroken cells were pelleted ($P_1$) by centrifugation at 500× g for 10 minutes at 4° C. The postnuclear supernatant ($S_1$) was centrifuged for 15 minutes at 20,000 rpm (SS 34 rotor) on a discontinuous Percoll density grandient, as described (8). Fractions of approximately 1 ml were collected at 4° C. and assayed for specific markers of azurophil granules ($\beta$-glucuronidase and myeloperoxidase), specific granules (vitamin B12-binding protein) and plasma membrane (alkaline phosphatase) as described below. Percoll was removed from pooled fractions by centrifugation at 35,000 rpm (180,000× g) for 2 hours in an SW41 rotor. The layer that sedimented above the packed Percoll was resuspended in relaxation buffer and stored in aliguots at −70° C.

Assays for Specific Markers in Subcellular Fractions

To ensure complete solubilization, aliquots of azurophil granules in relaxation buffer were diluted 1:5 in Triton X-100 (0.05% w/v final concentration) prior to enzyme or protein assays. Alkaline phosphatase was assayed with 1 mg/ml p-nitrophenyl phosphate as substrate in a 0.3 mM $MgCl_2$, 50 mM sodium barbital buffer, pH 10.5. 50 microliter samples diluted in Triton X-100 were assayed. Samples were incubated for 80 minutes at 37° C. in the assay mixture (1 ml volume) and the reaction was terminated by addition of 100 microliters of 1N NaOH. The absorbance at 410 nm was read immediately. The enzyme activity was calculated as described (10).

$\beta$-glucuronidase was assayed by liberation of phenolphthalein from 1 mM phenolphthalein $\beta$-monoglucuronic acid in 100 mM sodium acetate buffer, pH 4.4., at 37° C. for 3 hours. 25 microliter samples diluted in Triton X-100 were assayed in 550 microliters of assay mixture. The reaction was terminated by adding 200 microliters 1M glycine, 1M NaCl, 1M NaOH and the absorbance read at 550 nm. The enzyme activity was calculated as described (8).

Vitamin B12-binding protein was measured on 25-, 50- and 100 microliter samples diluted in Triton X-100 essentially as described (11). $^{57}$Co-Vitamin B12 was prepared by mixing 5 ng/ml vitamin B12 (Sigma) with 0.025 microcuries/ml $^{57}$Co-cyanocobalamin (Amersham, sp. act. $10^5$ cpm/ng). 750 microliters of saline were mixed with 350 microliters of $^{57}$Co-vitamin B12 and with 100 microliters final volume of the sample. 0.5 ml of albumin-coated charcoal was then added and the test tubes were centrifuged for 2 minutes at 10,000× g at room temperature. 1 ml of the supernatant was collected and counted in a Packard auto-gamma scintillation counter (Packard Instrument Co., Downers Grove, Ill.) to determine the amount of bound $^{57}$Co-B12 in each sample.

Protein was determined as described in (12) using bovine serum albumin as standard. To prevent Triton X-100 interference with the assay, 0.1% sodium dodecyl sulfate was added to the alkaline copper solution (13). Percoll at the concentration present in the fractions did not affect the assay.

To assay myeloperoxidase, 200 microliters of each fraction were diluted 5-fold in relaxation buffer containing 0.2% Triton X-100, and introduced into the sample compartment of a Perkin-Elmer 557 double beam spectrophometer (Coleman Instruments Divison, Oak Brook, Ill.). Absorption spectra, from 400 to 600 nm, of oxidized fractions versus fractions reduced with dithionite were then measured ($E_{472}$ nm=75 $mM^{-1}$ $cm^{-1}$) (14).

Preparation of an Azurophil-derived Bactericidal Factor (ADBF)

Fractions from the Percoll gradients corresponding to azurophil granules were pooled and Percoll was removed by centrifugation as described (8). The azurophil granule preparation was resuspended in relaxation buffer and stored either on ice at 4° C. or at −70° C. The azurophil granules stored on ice at 4° C. appeared to be intact in that no $\beta$-glucuronidase or myeloperoxidase release from the granules could be detected over 2 weeks. Freezing of the azurophil granules at −70° C. resulted in some leakiness (<20%) of the β-glucuronidase but not of the myeloperoxidase. The isolated azurophil granules were extracted with 0.05M glycine-HCl buffer pH 2.0 for 40 minutes at 25° C. The acid-extract was centrifuged at 10,000× g for 20 minutes and the supernatant used as a source of ADBF. The supernatant was either diluted in or dialysed against the incubation medium prior to bactericidal assays. For the dialysis of ADBF-extracts, a membrane tubing of 1,000 MR cut-off (Spectra/Por, Spectrum Medical, Los Angeles, Calif.) was used. Fractions from the Percoll density gradients were extracted following the same procedures; Percoll had no effect on the extraction or activity of the bactericidal factor.

Bactericidal Assays

Bactericidal activity was tested against *E. coli* K12 (MC 4100) in routine assays and, where indicated, against *Salmonella typhimurium* LT2, *Pseudomonas aeruginosa* PAC and PAO, *Listeria monocytogenes*, *Staphylococcus aureus*, and *Streptococcus pneumoniae* type III, type II and an unencapsulated variant of the *S. pneumoniae* type II strain. Trypticase soy broth and trypticase soy agar plates were used to cultivate most bacteria. In the case of *S. pneumonias*, Cy medium and 5% defibrinated sheep blood agar plates were used (15).

Organisms from a single colony on agar plates were inoculated into liquid medium and cultured overnight at 37° C. Aliquots of the overnight culture were inoculated into fresh nutrient broth and grown to mid-exponential phase. Bacterial cultures were then diluted into the test medium to the appropriate concentration. Most experiments were performed in 0.05M citrate buffer, pH 5.5. Control experiments showed that this buffer did not affect the viability of any of the bacteria tested except *P. aeruginosa* and *S. pneumoniae* type II, for which 0.05M phosphate buffer, pH 6.0 was used. Other buffers such as acetate, phosphate or citrate-phosphate at a concentration of 0.01M or 0.05M were used in some bactericidal assays, as specified below.

Bacteria ($4 \times 10^4$ colony-forming units in a final volume of 200 microliters) were incubated for 30 minutes at 37° C. with various amounts of azurophil granule extract (ADBF) or HL60 derived extract (BF) diluted in the incubation medium. Samples were then diluted 1:100 in M63 minimal medium (16), and spread onto agar plates. Colony forming units (CFU) were counted after incubation at 37° C. for 16 hours. Bactericidal activity was expressed as the percentage of bacteria killed after exposure to ADBF or BF compared to control. Alternatively, 1 unit of killing activity (K.U.) is defined as the reciprocal of the dilution of ADBF or BF preparation to kill $10^5$ bacteria/ml in 30 minutes at 37° C. ($LD_{50}$).

Fungicidal Assays

Fungicidal activity was tested against *Candida albicans* (clinical isolate from Columbia Presbyterian Hospital) in routine assays. Sabauraud broth and Sabauraud agar plates (Difco) were used to cultivate fungi.

Organisms from a single colony on agar plates were inoculated into liquid medium and cultured overnight at 37° C. Aliquots of the overnight culture were inoculated into fresh nutrient broth and grown to mid-exponential phase. Fungi cultures were then diluted into the test medium to the appropriate concentration. Experiments were performed in 10 mM phosphate buffer, pH 5.5.

*C. albicans* ($10^5$ colony-forming units/ml) were incubated for 60 minutes at 37° C. with various amounts of azurophil granule extract (ADBF) or HL60 derived extract (BF) diluted in the incubation medium. Samples were then diluted 1:100 in M63 minimal medium (16), and spread onto agar plates. Colony forming units (CFU) were counted after incubation at 37° C. for 30 hours.

Fungicidal activity was expressed as the percentage of fungi killed after exposure to ADBF or BF compared to control. Alternatively, 1 unit of killing activity (K.U.) is defined as the reciprocal of the dilution of ADBF or BF preparation necessary to kill $10^5$ fungi in 60 minutes at 37° C. ($LD_{50}$).

Isolation of Azurophil Granule Membranes

Isolated azurophil granules in relaxation buffer (pH 7.3) from neutrophil cells were disrupted by seven cycles of freezing in an acetone-dry ice bath and thawing at 37° C., followed each time by immersion for 10 seconds in a sonicating water bath (Bransen B3, Heat Systems-Ultrasonic Inc. Plainview, N.Y.). A pelleted material was then obtained by centrifugation of the lysed granules at 10,000× g for 60 minutes or at 135,000× g for 6 minutes at 4° C. This pelleted material was referred to as azurophil granule membranes. Isolated granule membranes and soluble granule contents were assayed for ADBF activity after incubation with 0.05M glycine pH 2.0 as previously described.

Characterization of ADBF by Size Exclusion Chromatography

Approximately 1 mg of ADBF membrane extract was applied to a Bio-Sil TSK-125 size exclusion column equilibrated in either 50 mM glycine/0.1M NaCl, pH 2.0 or 50 mM glycine/0.5M NaCl pH 2. ADBF bactericidal and fungicidal profiles and an O.D. 280 profile were generated from the eluted fractions. Sodium dodecyl sulfate-polyacrylamide gel electrophoresis (SDS-PAGE 15%) was performed on the ADBF membrane extract and on selected fractions obtained from the size exclusion column.

Characterization of ADBF by Reverse Phase High Performance Liquid Chromatography Trifluoroacetic acid (TFA) was added to ADBF or TSK purified ADBF to 0.1% and the samples were applied to a Vydac wide pore $C_4$ (250×4 mm) reverse phase column and run on a 92 minute gradient, followed by 3 minutes at 100% and then a 2 minute wash. Solvent A was 0.1% aqueous TFA, solvent B was 0.1% TFA in HPLC grade acetonitrile. The gradient was as follows:

| TIME % | SOLVENT B |
|---|---|
| 0–2 minutes | 0% |
| 2–62 minutes | 0–48% |
| 62–92 minutes | 48–100% |
| 92–95 minutes | 100% |
| 95–97 minutes | 0% |

The equipment utilized was a Beckman reverse phase HPLC system consisting of a Vydac wide pore $C_4$ (250×4 mm) reverse phase column, two 110B pumps, a 421A controller, a 210A injector, a 2 ml sample loop, a 163 variable wavelength detector, a 2112 Redirac fraction collector, and a Kipp and Zonen BD 41 chart recorder. The detector setting was 214 nm, 0-0.5 absorbance units full scale (AUFS) and the peak fractions were collected manually.

Sequence Analysis of Polypeptides Derived From ADBF

RPHPLC purified ADBF and TSK/RPHPLC purified ADBF were concentrated to 50 microliters on a Speed Vac® and loaded onto an Applied Biosystems 477A pulse liquid phase sequenator. Phenylthiohydantoin (PTH) analysis was performed on line using an Applied Biosystems Model 120A PTH Analyzer.

Amino Acid Analysis of Polypeptides Derived From ADBF

PTC amino acid analysis of polypeptides was obtained by 1 hour hydrolysis with 6.0N HCl at 150° C. using a Waters Picotag® system equipped with a Beckman HPLC system.

Culturing HL60 Cells

HL60 cells (39, 40) were grown in suspension cultures containing basal media (serum free) supplemented with insulin and transfertin. Cells were grown to a density of $2 \times 10^6$ cells/ml and harvested by centrifugation. The cell pellet was resuspended to $1 \times 10^8$ cells/ml for further fractionation.

Subcellular Fractionation of HL60 Cells

HL60 cells in phosphate-buffered saline ($2 \times 10^7$ cells/ml) were treated with 5 mM DFP for 15 minutes at 4° C. The DFP-treated cells were centrifuged at $130 \times$ g for 10 minutes at 4° C., and the resulting pellet was resuspended in ice-cold relaxation buffer containing 100 mM KCl, 3 mM NaCl, 1 mM ATP (Na)2, 3.5 mM $MgCl_2$, and 10 mM Pipes, pH 7.3. The cell suspension was disrupted by nitrogen cavitation for 20 minutes at 350 psi in a bomb at 4° C. and the cavitate was collected into the $Ca^{2+}$ ion chelator EGTA, pH 7.4, at a final concentration of 1.5 mM. Nuclei and unbroken cells were pelleted ($P_1$) by centrifugation at $500 \times$ g for 10 minutes at 4° C. The postnuclear supernatant ($S_1$) was centrifuged for 30 minutes at $10,000 \times$ g to pellet granules. This crude granule preparation was resuspended in relaxation buffer and stored in aliquots at $-70°$ C. Alternatively, the postnuclear supernatant ($S_1$) was centrifuged for 15 minutes at 20,000 rpm (SS 34 rotor) on a discontinous Percoll density gradient, as described (8). Fractions of approximately 1 ml were collected at 4° C. and assayed for specific markers of azurophil granules ($\beta$-glucuronidase and myeloperoxidase), specific granules (vitamin B12-binding protein) and plasma membrane (alkaline phosphatase) as described above. Percoll was removed from pooled fractions by centrifugation at 35,000 rpm ($180,000 \times$ g) for 2 hours in an SW41 roter. The layer that sedimented above the packed Percoll was resuspended in relaxation buffer and stored in aliquots at $-70°$ C.

Preparation of an HL60 Derived Bactericidal Factor (BF)

Fractions from either the Percoll gradients corresponding to myeloperoxidase activity or the crude granule preparation from HL60 cells were resuspended in buffer and stored either on ice at 4° C. or at $-70°$ C. The crude granule preparation or the isolated granules were extracted with 0.05M glycine-HCl buffer pH 2.0 for 40 minutes at 25° C. The acid-extract was centrifuged at $10,000 \times$ g for 20 minutes and the supernatant was either diluted or dialyzed against the incubation medium prior to bactericidal assays. For the dialysis of BF extracts, a membrane tubing of 1000 $M_r$ out-off (Spectra/For, Spectrum Medical, Los Angeles, Calif.) was used.

Preparation and Screening of HL60 cDNA Libraries

Human HL60 cells (ATCC CCL 240) were grown as specified to $1 \times 10^6$ cells/ml in DMEM containing 5% fetal calf serum. For the induced library, cells were treated with 1% DMSO 40 hours prior to harvest. The cells were harvested at 4° C. and washed twice with phosphate-buffered saline (PBS). The cell pellets were recovered, homogenized in buffer containing 20 mM vanadyl complex (Bethesda Research Laboratories) and 0.2% Nonidet P-40, and centrifuged for 10 minutes at 14,000 rpm in a Beckman JS-13 rotor. RNA was prepared from the supernatant using phenol-chloroform extraction and the total RNA obtained was subjected to oligo-dT affinity chromatography to obtain mRNA.

The total mRNA preparations from the induced and uninduced cells were used as a template to prepare cDNA libraries in $\lambda$gt10, as described in (41), but with second strand synthesis performed according to the method described in (42). The resulting cDNA was ligated with a synthetic oligonucleotide (CCGGAATTCCGG, Bethesda Research Laboratories) and then digested with EcoR1. The cDNA was size fractionated and purified using polyacrylamide gels and inserted into the EcoR1 site of $\lambda$gt10. Several million phage were obtained from both induced and uninduced RNA. Triplicate filter lifts were prepared and phage were screened under conditions of moderate stringency ($6 \times$ SSC, 35° C.) with a 5'-end labeled mixture of a 14 mer pool of 16 oligonucleotides prepared using the reverse complement of the sequence encoding amino acids 31-35 of peak 5b. (see FIG. 14).

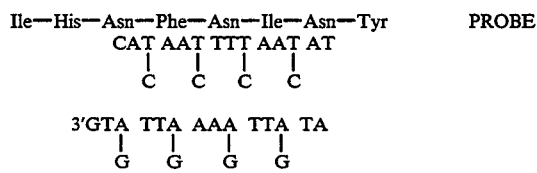

Results

Subcellular Distribution of Bactericidal Factor

Figure 1A:
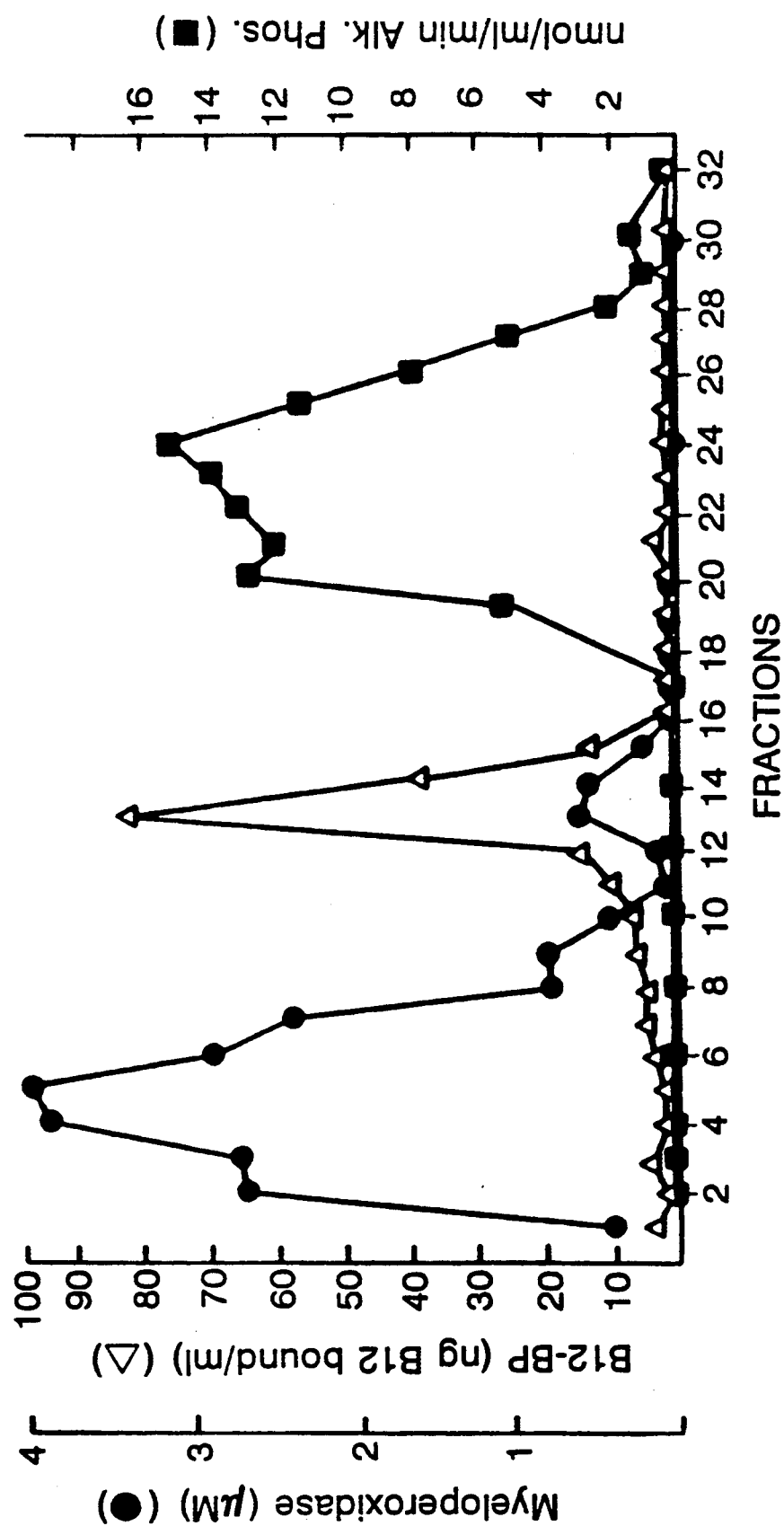
FIGS. 1A, 1B and 1C. Subcellular distribution of bactericidal activity in human neutrophils FIG. 1(A) Distribution of markers for azurophil granules (myeloperoxidase), specific granules (vitamin B12-binding protein), and plasma membrane (alkaline phosphate).
Figure 1B:
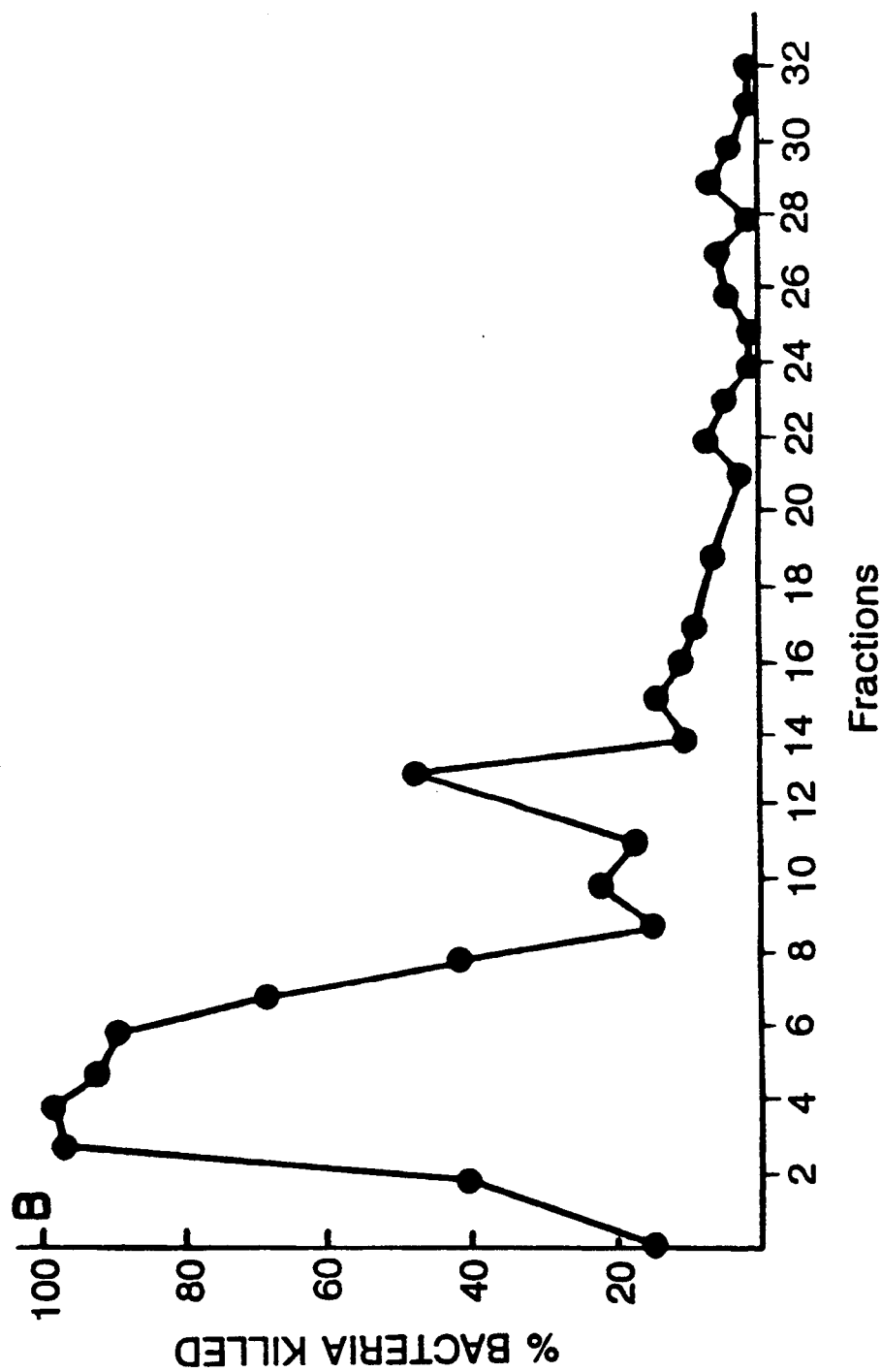

To determine the subcellular location of ADBF in neutrophils, the neutrophils were fractionated using the method described (8). Neutrophils were treated with 5 mM diisopropylfluorophosphate (DFP) prior to fractionation because DFP, a potent serine protease inhibitor, has been shown to inhibit proteolysis very effectively in PMN extracts (17, 18). $10^9$ DFP-treated cells were disrupted by nitrogen cavitation, and the postnuclear supernatant was centrifuged on a discontinuous Percoll density gradient. Each fraction of the gradient was assayed for specific markers of azurophil granules (myeloperoxidase), specific granules (vitamin B12-binding protein) and plasma membrane (alkaline phosphatase). As shown in FIGS. 1A and 1B, the method resulted in efficient separation of these three compartments. Azurophil granules showed no contamination by markers of specific granules or plasma membranes. Specific granules were not contaminated by plasma membranes but had some contamination by azurophil granules, as indicated by the presence of 10% of the myeloperoxidase in this peak.

Bactericidal activity, obtained by extraction of cellular fractions at pH 2.0, distributed as shown in Table I.

TABLE I

Distribution of BF in Human Neutrophils

| Purification step | Volume (ml) | Protein (mg/ml) | K.U.[a] | S.A.[b] | Yield (%) |
|---|---|---|---|---|---|
| Cavitate | 9.8 | 0.6 | 1500 | 2500 | 100 |
| Pellet | 2.0 | 0.6 | 450 | 750 | 6 |
| S1[c] | 8.8 | 0.46 | 1280 | 2780 | 97 |
| S2[d] | 8.0 | 0.26 | 6.5 | 25 | 0.8 |
| γ (plasma membrane) | 3.0 | 0.13 | 4.0 | 30 | 0.4 |
| β (specific granules) | 3.0 | 0.21 | 2.5 | 12.5 | 4.5 |
| α (azurophil granules) | 3.0 | 0.20 | 1430 | 7140 | 86 |

Figure 1C:
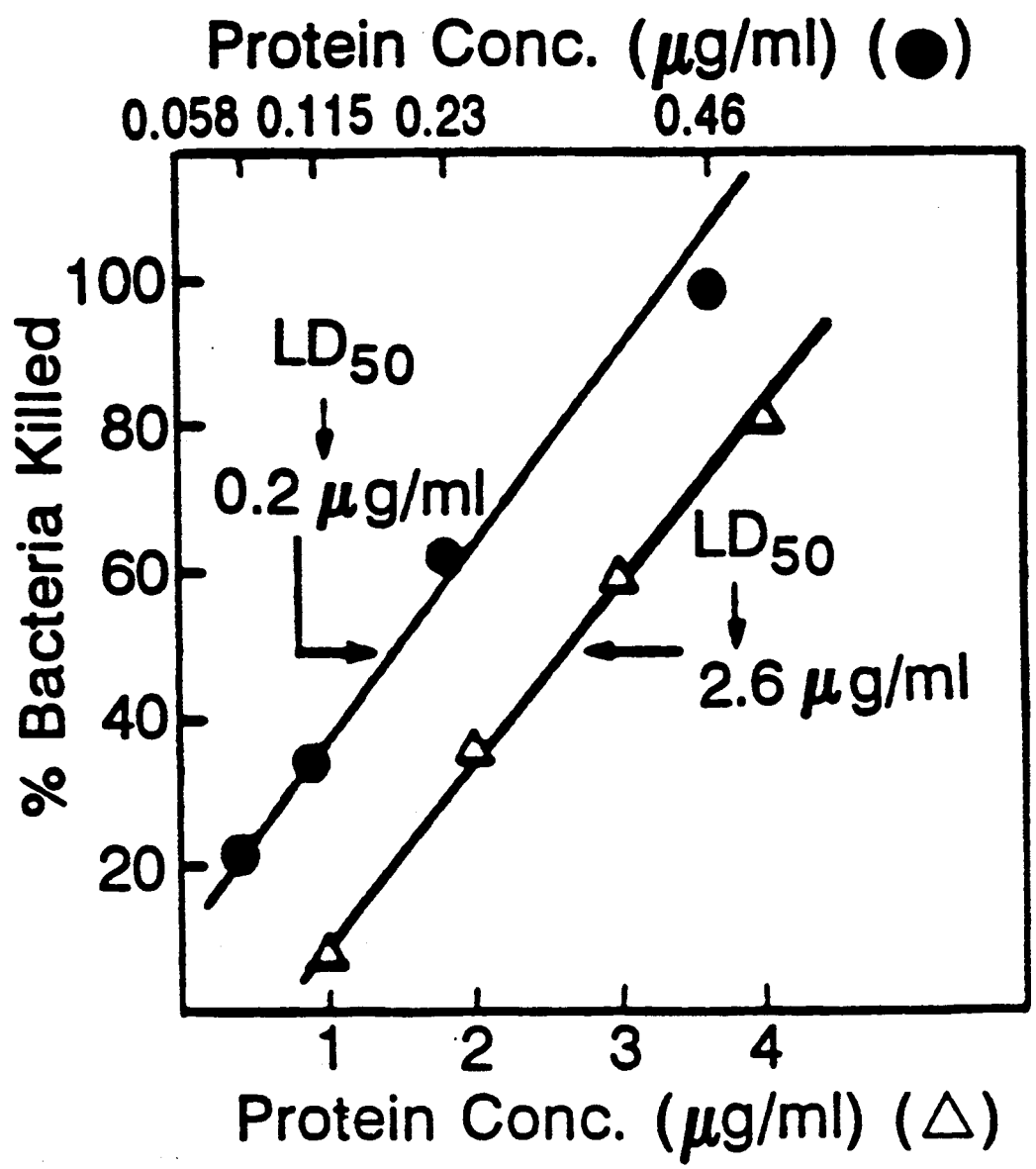

[a]Killing units
[b]Specific activity (KU/mg protein)
[c]Postnuclear supernatant
[d]Cytosol The majority of activity of the cavitate was present in the postnuclear supernatant (S1). 6% of activity was associated with the nuclear fraction, perhaps due to adherence of a few granules to nuclei. The location of the bactericidal factor in the granule fraction was further indicated by a specific activity which was twice that of the unfractionated cavitate. As shown in FIG. 1, more than 90% of the bactericidal factor was present in the azurophil granule fraction. The low level of activity present in the specific granule fraction could be attributed to the 10% contamination by azurophil granules, as detected by the myeloperoxidase assay (see FIGS. 1A and 1B). Indeed, approximately 10 times more protein from the specific fraction than from the azurophil granule fraction was required to kill 50% of the bacteria (inset, FIGS. 1A and 1B).

Figure 2:
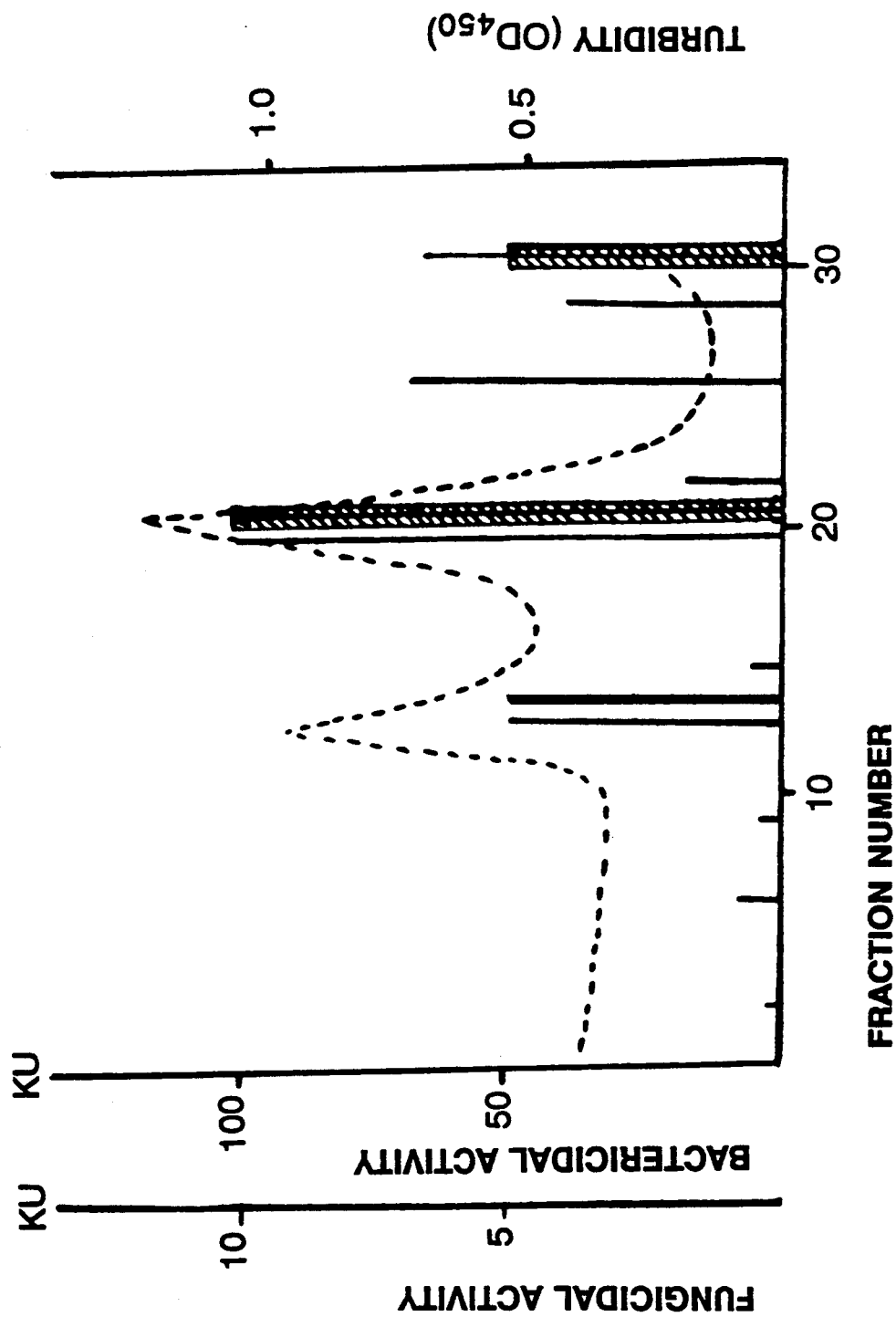
FIG. 2. HL60 postnuclear supernatant Percoll gradient bactericidal and fungicidal activity profiles (- - -) = turbidity ($OD_{450}$)

To determine the subcellular location of BF in HL60 cells, DFP treated HL60 cells were fractionated as described for DFP treated neutrophils. Each fraction of the Percoll gradient was assayed for bactericidal activity and fungicidal activity. As shown in FIG. 2, the granule profile from HL60 cells differs from the granule profile of neutrophils, possibly reflecting that HL60 cells are undifferentiated neutrophil precursor cells. Bactericidal and fungicidal activities were greatest in fractions 20–22. These fractions also correspond to the highest concentrations of myeloperoxidase activity.

Membrane Association of Bactericidal Factors

To determine the location of ADBF within neutrophil azurophil granules, intact purified granules were lysed at neutral pH by repeated freeze-thaw and sonication. The disrupted granules were centrifuged and soluble granule contents were separated from pelleted granule membranes. Under these conditions, more than 90% of β-glucuronidase and myeloperoxidase were found in the supernatant fraction (data not shown). In contrast, 98% of ADBF was associated with azurophil membranes, as shown in FIG. 3. Examination of crude granule extracts from HL60 cells have also indicated membrane association of BF (data not shown).

The ability of a number of agents to release ADBF from azurophil membranes was also examined. ADBF activity was assayed in the supernatant, and the pellet obtained after centrifugation of azurophil membranes was treated with buffers of varying pH. FIG. 4 shows that less than 10% of ADBF activity was released from the membrane at pH 5.0–7.0, 50% at pH 4.0 and 100% at pH 2.0–3.0. The extraction of the bactericidal factor from intact azurophil granules followed the same pH curve (data not shown). Other agents commonly used to solubilize peripheral and integral membrane proteins were then tested (see Table II below). 50 microliters of azurophil membranes (0.5 micrograms protein/microliters) were incubated at 25° C. for 40 minutes in 200 microliters of the various agents above. After centrifugation at 10,000× g for 20 minutes (4° C.), the supernatants were collected, dialysed against 0.05M citrate pH 5.5 and tested for protein and bactericidal activity. Pellets were washed 3 times with ice-cold 0.05M phosphate pH 7.0, incubated at 25° C. for 40 minutes with 0.05M glycine pH 2.0, centrifuged and the supernatants assayed for protein and killing activity. For Triton X-114 treatment of azurophil membranes, the procedure described in (19) was followed.

TABLE II

Effect of pH, Ionic Strength and Surface-Active Agents on the Release of ADBF from the Azurophil Membrane

| Azurophil membranes treated with: Buffer | Additional Agents | Bactericidal activity of material released into supernatant (killing units) | Bactercidial activity of material remaining in membrane pellet (killing units) |
|---|---|---|---|
| 0.05 M glycine pH 2.0 | — | 1430 | <10 |
| 0.05 M citrate pH 5.5 | — | 20 | 1190 |
| 0.1 M sodium bicarbonate, pH 11.0 | — | <10 | 1100 |
| 0.05 M phosphate pH 7.0 | 2 M NaCl | <10 | 820 |
| None | 6 M urea | <10 | 1310 |
| 0.05 M phosphate pH 7.0 | 1% Triton X-100 | 1310 | <10 |
| 0.01 M Tris pH 7.4 | 0.15 M NaCl 0.05% Triton X-114 | 170[a] 1200[b] | N/A[c] |

[a]aqueous phase
[b]detergent phase
[c]not applicable

As shown in Table II, treatment of the azurophil membranes with 1% Triton X-100 released ADBF activity as effectively as acid. In contrast, neither 6M urea nor 0.1M sodium bicarbonate pH 11 released the bactericidal factor from the granule membrane.

Triton X-114 has been used on isolated membranes or whole cells to separate integral membrane proteins from hydrophilic proteins; hydrophilic proteins are recovered in the aqueous phase, whereas amphiphilic integral membrane proteins are found in the detergent phase after the phase separation of this detergent at 20° C. and greater (19, 20). When azurophil membranes were extracted with Triton X-114, 87% of ADBF activity partitioned with the detergent phase.

ADBF-activity in vitro Depends on Release from the Azurophil Membrane

Azurophil membranes were treated at pH 2.0, which solubilizes ADBF, or at pH 5.5, which represents intralysosomal pH (21-23) but does not release ADBF from the membrane (see FIG. 4). Bactericidal activity was then assayed at pH 5.5 in total membranes, and in the supernatant and pellet fractions obtained after centrifugation of the membranes treated at both pH's. ADBF from membranes treated at pH 5.5 (membrane-bound ADBF: 1 K.U.) was 10 times less active than ADBF from membranes treated at pH 2.0 (soluble ADBF: 11.6 K.U.). Bactericidal activity could be recovered almost completely from membranes treated at pH 5.5 by reextraction at pH 2.0 (see Table II above).

Effect of Dose, Time, Bacterial Growth Status, and Buffer

ADBF activity was linear with respect to protein concentration over the range of 0.3 to 30 micrograms/ml (FIG. 1 and further data not shown). The effect of bacterial concentration is shown in FIG. 5: up to $10^7$ bacteria/ml could be killed by 30 micrograms/ml of ADBF-containing extract in 30 minutes at 37° C. Killing was rapid: 50% of the cells were killed within 5 minutes at 37° C. by the azurophil granule extract containing 1.4 micrograms protein/ml (FIG. 6). The physiological state of the bacteria incubated in the test medium did not affect their susceptibility to ADBF. Thus, bacteria in exponential growth or in stationary phase were equally sensitive. The addition of glucose (20 mM) to the incubation medium did not affect ADBF activity. The killing activity of ADBF was approximately the same when citrate, acetate or phosphate salts were used as a buffer (data not shown).

Effect of pH and Divalent Cations

Since it has been shown that phagosomes rapidly reach and maintain a pH value of 5.5 during intracellular killing of bacteria in vivo (21-23), the effect of pH on the bactericidal activity of ADBF and BF in vitro was examined. ADBF and BF were effective over a broad range of pH (5.0 to 8.0) (FIGS. 7 and 8, respectively). Media more acidic than pH 5.0, which are bactericidal per se, could not be used to test ADBF killing.

Because ions such as $Mg^{2+}$ and $Ca^{2+}$ play a critical role in phagocytic processes (24) and also affect the surface properties of Gram-negative bacteria (25), the effect of these ions on ADBF and BF bactericidal activity was also examined. $Mg^{2+}$ ions antagonized but did not completely block ADBF activity. The effect of $Mg^{2+}$ ions was maximal at 1 mM, with a 25% reduction in bactericidal activity (data not shown). In contrast, $Ca^{2+}$ ions inhibited all ADBF and BF activity at a concentration of 25 mM and 20 mM (FIGS. 9 and 10 respectively). The decrease of bactericidal activity was roughly linear with respect to calcium concentration over the range of 1 to 25 mM. Since the medium used for these tests contains citrate, which chelates divalent cations, the concentration of free cations in solution is lower than the nominal concentration. However, citrate does not bind significant amounts of magnesium and calcium at low pH (26). The addition of EDTA (1-25 mM) to the incubation medium (to chelate cations) did not affect ADBF or BF activity (data not shown). Sodium chloride inhibited at a concentration of 0.3M or greater (FIG. 11). Physiological concentrations of sodium chloride or potassium chloride did not inhibit ADBF activity when the latter was tested at a concentration of 2.8 micrograms/ml or greater.

Bacterial Spectrum of ADBF Killing

ADBF kills both Gram positive and Gram negative bacteria (see Table III below).

TABLE III

| Antibacterial Spectrum of ADBF | | |
|---|---|---|
| Organism | Strain or Type | ADBF Activity[a] |
| *Staphylococcus aureus* | S27 | + |
| *Staphylococcus aureus* | 450 | + |
| *Staphylococcus aureus* | TSS-1[b] | + |
| *Staphylococcus aureus* | TSS-2[b] | + |
| *Streptococcus pneumoniae* | Type III | — |
| *Streptococcus pneumoniae* | Type II | + |
| *Streptococcus pneumoniae* | R6 | + |
| *Listeria monocytogenes* | 450 | (+) |
| *Pseudomonas aeruginosa* | PAC | + |
| *Pseudomonas aeruginosa* | PAO 103-0 | + |
| *Salmonella typhimurium* | LT2 | + |
| *Escherichia coli* K12 | MC 4100 | + |

[a]ADBF activity is scored according to the microgram/ml of protein in azurophil extract necessary to kill $10^5$ bacteria in 30 minutes at 37° C.: +, 0.1 to 0.3 micrograms/ml; (+), 1 to 2.5 micrograms/ml; —, 20 micrograms/ml.
[b]Clinical isolates from two patients with toxic shock syndrome.

The Gram positive bacteria susceptible to ADBF killing included different strains of *Staphylococcus aureus* (two isolates from patients with toxic shock syndrome), β-hemolytic streptococci (with the exception of the capsulated streptococcus type III) and to some extent *Listeria monocytogenes*. All the Gram negative bacteria tested were killed as efficiently as *E. coli*.

Fungicidal Acitivity of ADBF

FIG. 12 shows that ADBF has fungicidal activity within the range from about 3.0 micrograms/ml to about 16.0 micrograms/ml.

Purification of ADBF

Reverse phase high performance liquid chromatography (RPHPLC) of the ADBF extract resulted in a reproducible profile containing at least 9 characteristic peaks, some of which appear as doublets (see FIG. 13A). When a portion of each fraction was dried to remove the reverse phase solvents and then subsequently resuspended and assayed, two peaks of activity were identified as shown by the cross-hatched areas of FIG. 13A. The first activity peak overlaps two major UV peaks, designated peak 5 and peak 6, the second activity peak is associated with a single UV peak, designated peak 9. The amino acid sequence of peak 5 revealed two proteins, one with sequence identity to lysozyme (5a) and another (5b) with the N-terminal sequence shown in FIG. 14. Peak 6 contained a single novel sequence with homology to the trypsin superfamily (see FIG. 14). Peak 9 contained at least 2 proteins, i.e., 9a and 9b, having the sequences shown in FIG. 14.

Because the sequences designated 5b and 9b are identical and because both peaks are associated with bactericidal activity, applicants contemplate that this sequence along with that of 9a, is responsible for such bactericidal activity.

ADBF activity was partially purified by size exclusion chromatography on a Bio-Sil TSK-125 column as shown in FIG. 15. Fungicidal and bactericidal activity coeluted on the column with two peaks of activity, the major peak migrating within the 50-60 kD region (fractions 31 and 32) and the minor peak within the 10-20 kD region (fraction 42). The starting material for TSK size exclusion chromatography (ADBF) and various TSK size exclusion chromatography fractions were analyzed by polyacrylamide gel electrophoresis (15%) as shown in FIG. 16.

RPHPLC of the 50-60 kD size exclusion peak (fractions 31-32) resulted in 2 peaks of activity, a minor activity peak associated with the region including peaks 4, 5, and 6, and a major activity peak associated with peak 9 (FIG. 13B). Amino acid sequence analysis of peak 4 shows identity to human cathepsin G (see FIG. 14). Peak 9 corresponded to a single N-terminal sequence designated 9a in FIG. 14. Amino acid composition of purified peak 9a is shown in Table IV below.

TABLE IV

| Amino Acid Analysis of Purified Peak 9a | |
|---|---|
| Amino Acid | Mole (%) |
| Asp | 7.3 |
| Glu | 7.4 |
| Ser | 8.8 |
| Gly | 7.3 |
| His | 1.8 |
| Arg | 4.7 |
| Thr | 4.2 |
| Ala | 11.2 |
| Pro | 6.2 |
| Tyr | 2.6 |
| Val | 8.1 |
| Met | 2.5 |
| Ile | 5.1 |
| Leu | 10.4 |
| Phe | 5.5 |
| Lys | 7.3 |

SDS-PAGE (10%) analysis of peak 9 shows the major protein band to have a molecular weight of approximately 54,000 daltons (FIG. 17).

RPHPLC of the 10-20 kD size exclusion peak (fraction 42) resulted in a single activity peak associated with peak 5 (FIG. 13C) and having a single n-terminal sequence identical to 5b (FIG. 14). SDS-PAGE analysis of peak 5 revealed a single band on SDS-PAGE with an apparent molecular weight of 13,000 daltons (see FIG. 18).

Improved resolution was obtained with TSK size exclusion chromatography using a buffer consisting of 50 mM glycine pH 2, 500 mM NaCl (see FIG. 21). Under these conditions, virtually complete separation of the 54 kD band was obtained from the 29 kD bands. Activity profiles indicated that the 54 kD protein (fractions 34-36) demonstrated only bactericidal activity and no antifungal activity. A region containing predominantly two proteins of 13 kD and 18 kD (fractions 42-45) contained most of the antifungal activity in addition to bactericidal activity. FIG. 22 shows the SDS-PAGE results corresponding to the various fractions.

HL60-derived BF was purified from granules (collected after Percoll gradient centrifugation) by TSK size exclusion chromatography and RPHPLC as described for ADBF. RPHPLC (FIG. 19) revealed a peak of activity which upon sequence analysis, corresponded to sequence 9a (FIG. 14) with some contamination of elastase (peak 8).

Human HL60 cDNA libraries were screened with a probe derived from the sequence comprising amino acids 31-35 of peak 5b as described hereinabove. 16 clones were plague-purified from the induced library. Each clone was digested with the enzyme Sau3a and the fragments inserted into the single-strand phage M13. Phage were screened by hybridization to the 14 mer pool and positive M13 phage were sequenced using the dideoxy chain termination method as described in (43). One of these clones, P-7, contained a sequence which matched exactly with that predicted by the protein sequence up to a point between amino acid residue 13 and 14 where the synthetic oligonucleotide was inserted. The EcoR1 fragment of clone P-7 was used to rescreen the uninduced libarary, from which 8 cDNA clones were isolated. One of these clones, designated P-FL2, was inserted into M13 vectors and sequenced. A second cDNA clone (P-FL1) was also sequenced. It was identical to P-FL2 except that its 5' end began at a point 43 base pairs after the 5' end of clone P-FL2.

Both clones (P-FL1 and P-FL2) contain identical open reading frames encoding 220 amino acids with a predicted molecular weight of 24,823 (FIGS. 20A and 20B). One N-linked glycosylation site is present (Ash-85) which could result in a larger molecule. Residues $Thr_{105}$-$Ile_{144}$ correspond exactly to the amino terminal sequence obtained for peak 5b. The predicted molecular weight for the C-terminal portion of the molecule ($Thr_{105}$-$Tyr_{220}$) is 12,867, similar to the apparent molecular weight of peak 5b on SDS-PAGE.

Discussion

Since the early studies by Hirsch (27-29), various bactericidal proteins have been described and in some cases isolated from neutrophils (7, 18, 30-34). The subcellular location of these or other human neutrophil-derived bactericidal proteins has not been established. As disclosed herein, human neutrophils were treated with DFP to prevent proteolysis. These treated neutrophils were fractionated using a scheme which results in clear separation of cytosol, plasma membrane, specific granules, and azurophil granules, with minimal proteolysis or alteration of granule integrity and density. Optimum conditions for the extractions and assay of ADBF were determined; ADBF was maximally extracted at pH 2.0-3.0 and assayed at pH 5.5 (phagolysosomal pH). Under these conditions, all cellular compartments were screened and it was found that most of the bactericidal activity (97%) was associated with the postnuclear supernatant ($S_1$) while approximately 90% of the activity comigrated with the azurophil granule population after centrifugation of $S_1$ on Percoll density gradients. Neither the cytosol nor the plasma membrane fractions had significant activity. The low level of activity (5-10%) in the specific granule fraction could be accounted for by the 5-10% contamination of this fraction by myeloperoxidase-positive azurophil granules. The data showed a single location for human neutrophil BF, namely, the azurophil granule.

In support of these results, a single location for ADBF was found in human neutrophils, where bactericidal activity was exclusively localized to a large myeloperoxidase-positive granule population (35). In addition, it has been reported that one of the neutrophil-derived bactericidal factors (BPI) can be recovered (90%) in the cellular fractions containing azurophil granules (36). In contrast, Rest et al. (37) found a bactericidal factor in both azurophil and specific granules of human neutrophils. Since they used a different technique of fractionation (homogenization in sucrose and isopycnic centrifugation on sucrose density gradients), as well as different methods of extraction and assay, their results are not directly comparable with the results described herein.

ADBF is associated with the azurophil membrane. Upon lysis of azurophil granules at neutral pH, which solubilized 90% of the myeloperoxidase, 90% of ADBF remained in the membrane containing pellet. All of the membrane-associated ADBF could be extracted at pH 2.0 and released in soluble form after centrifugation of the acid-treated membrane. Possible explanations for the solubilizing effect of acid are: (1) acid induces a proteolytic event; (2) acid induces conformational changes which disrupt the association of ADBF with the granule membrane; or (3) acid displaces a charge interaction between ADBF and the membrane. Low pH was not strictly required for solubilization of ADBF. Triton X-100 at neutral pH could also release ADBF. Agents commonly used to solubilize peripheral membrane proteins, such as 2M NaCl, 6M urea or 0.1M sodium bicarbonate pH 11, were unable to dissociate ADBF from the azurophil membrane. This indicates that ADBF is either tightly associated with or comprises an integral constituent of the azurophil membrane. Indeed, upon treatment of azurophil membranes with Triton X-114, ADBF behaved like an integral membrane constituent, in that it partitioned into the detergent phase.

The question of whether the release of a bactericidal factor from the membrane is necessary for bactericidal activity was also addressed. Membrane-bound ADBF was 10 times less active than soluble ADBF, suggesting a coupling in vitro between ADBF solubilization and activity. The molecular mechanism of ADBF activation in vivo is yet to be understood.

On the basis of the localization results described herein, intact, purified azurophil granules were used as a source of ADBF and their properties studied. This contrasts to previous work in which bactericidal proteins were obtained from an heterogeneous granule-enriched fraction, by extraction with acid over long periods of time (7, 18, 31) in the absence of protease inhibitor (7, 31). ADBF resembles some of the bactericidal proteins previously described in being acid-extractable and granule-associated. In particular, ADBF shares many of the characteristics of the rabbit neutrophil-derived phagocytin (28, 29, 38): (1) Changes in the test medium such as a variation in the buffer, the addition of glucose, and inclusion of a metal binding agent has little effect on the bactericidal activity of ADBF; and (2) Divalent cations ($Mg^{++}$, $Ca^{++}$) were not required for its lethal action (at high concentration, these ions antagonized or, in the case of $Ca^{++}$, inhibited completely the bactericidal effect -$ID_{50}$ for $Ca^{++}=10$ mM). Like phagocytin, ADBF was more active at a low pH (5.0–5.5), the estimated phagolysosomal pH during intracellular killing of bacteria.

ADBF differs from other reported neutrophil-derived antimicrobial proteins in a number of ways. ADBF is active over a wide range of pH, with optimum activity at pH 5.5, and is relatively insensitive to high ionic strength. This contrasts with bacterial permeability increasing factor (BPI), which is optimally active at pH 7.0, and defensins, which strictly require pH 7.0–8.0 and low ionic strength conditions for bactericidal activity (7, 31, 34, 35). By its antimicrobial spectrum, ADBF differs from purified factors such as BPI or cationic antimicrobial proteins, which are only active on Gram-negative bacteria (18, 31, 34).

ADBF is extremely active: 0.1 to 0.3 micrograms/ml can kill $10^5$ bacteria per ml, using a wide range of test organisms—Gram-positive and Gram-negative bacteria. Purified bactericidal factors specific for Gram-negative bacteria, such as BPI (31,44) and the 57 kD cationic antimicrobial protein (18) have comparable activity, whereas others, such as defensins, seem to be active only at higher concentrations (50 micrograms/ml) on both Gram-positive and Gram-negative bacteria (7, 34). In addition, ADBF kills bacteria rapidly: more than 50% killing is achieved within 5 minutes. Moreover, ADBF killing does not appear to involve $H_2O_2$-dependent systems, since catalase (500 U/ml) does not significantly reduce its activity (data not shown) and since greater than 90% myeloperoxidase is released in the soluble fraction upon isolation of membrane-ADBF.

Chromatography of ADBF on reverse phase HPLC reveals 9 major protein peaks encompassing at least 10 different polypeptides. Several contain amino-terminal sequences identical to known polypeptides, including:

| | |
|---|---|
| Peak 1 | Defensin |
| Peak 4 | Cathepsin G |
| Peak 5a | Lysozyme |
| Peak 8 | Elastase |
| Peak 9a | Bactericidal/Permeability Increasing Protein (BPI) |

Activity profiles across reverse phase chromatography fractions of azurophil granule extract and partially purified ADBF associated killing of E. coli, with peaks 5b and 9a. Thus, two purified polypeptides with distinct amino terminal sequences can be identified. BPI, as described in the literature (31,44), is only active against Gram negative bacteria.

From the amino acid sequence derived from peak 5b, a novel full length cDNA was cloned which encodes a 220 amino acid polypeptide, with a predicted molecular weight of 24,823 daltons. This protein represents a precursor to the 13 kD polypeptide described by peak 5b which may be processed in the neutrophil or during purification. The fact that the sequence of peak 5b also appears in peak 9 (designated sequence 9b in FIG. 14) could be explained in several ways: 1) C-terminal degradation; 2) conformational differences or 3) post column processing of an N-terminally blocked precursor.

Because mature polymorphonuclear leukocytes cannot be grown for an extended period of time in culture, the use of neutrophil precursor cells for production of bactericidal factors was investigated. Investigation of HL60 cell derived bactericidal factor (BF) revealed a different granule profile than obtained from neutrophils after separation on Percoll gradients. However, a peak of bactericidal and fungicidal activity was present that overlapped the peak of myeloperoxidase activity (a marker of azurophil granules in mature neutrophils). The activity of HL60 derived BF is essentially identical to ADBF in its potency (nanograms per milliliter required to kill a fixed number of bacteria), pH activity profile, sensitivity to $CaCl_2$, migration on Superose 12 FPLC size exclusion chromatography and membrane association. Thus, the production of BF from HL60 cells provides an alternative means of generating large quantities of BF for commerical use.

REFERENCES

1. Klebanoff, S. J. and R. A. Clark. 1978. *The Neutrophil: function and clinical disorders*. North-Holland Publishing Company. pp. 1–810.

2. Kaplan, E. L., T. Laxdal, and P. G. Quie. 1968. Studies of polymorphonuclear leukocytes from patients with chronic granulomatous disease of childhood: Bactericidal capacity for streptococci. Pediatrics 41: 591–599.
3. Mandell, G. L. 1974. Bactericidal activity of aerobic and anaerobic polymorphonuclear neutrophils. Infect. Immun. 9: 337–341.
4. Elsbach, P., and J. Weiss. 1983. A reevaluation of the roles of the O2-dependent and O2-independent microbicidal systems of phagocytes. Rev. Infect. Dis. 5: 843–853.
5. Spitznagel, J. K., and W. M. Shafer. 1985. Neutrophil killing of bacteria by oxygen-independent mechanisms: A historical summary. Rev. Infect. Dis. 7: 398–403.
6. 2Ganz, T., M. E. Selsted, D. Szklarek, S. S. L. Harwig, K. Daher, D. F. Bainton and R. I. Lehrer. 1985. Defensins, natural peptide antibiotics of human neutrophils. J. Clin. Invest. 76: 1427–1435.
7. Selsted, M. E., S. S. L. Harwig, T. Ganz, J. W. Schilling and R. I. Lehrer. 1985. Primary Structures of Three Human Neutrophil Defensins. J. Clin. Invest. 76: 1436–1439.
8. Borregaard, N., J. M. Heiple, E. R. Simons, and R. A. Clark. 1983. Subcellular localization of the b-cytochrome component of the human neutrophil microbicidal oxidase: translocation during activation. J. Cell Biol 97: 52–61.
9. Boyum, A. 1968. Separation of leukocytes from blood and bone marrow. Scand. J. Clin. Lab. Invest. 21 (Suppl.): 77–89.
10. Lindhardt, K. and K. Walter. 1963. Phosphatases (phosphomonoesterases). In Methods of Enzymic Analysis. H.-U. Bergmeyer, editor. Academic Press, Inc., New York. 779–787.
11. Gottlieb, C., K.-S. Lau, L. R. Wasserman, and V. Herbert. 1965. Rapid charcoal assay for intrinsic factor (IF), gastric juice unsaturated B12 binding capacity, antibody to IF, and serum unsaturated B12 binding capacity. Blood 25: 875–893.
12. Lowry, O. H., N. J. Rosebrough, A. L. Fart, and R. J. Randall. 1951. Protein measurement with the Folin phenol reagent. J. Biol. Chem. 193: 265–275.
13. Wang, C. S. and R. L. Smith. 1975. Lowry determination of protein in the presence of Triton X-100. Anal. Biochem. 63: 414–417.
14. Bos, A., R. Wever, and D. Roos. 1978. Characterization and quantification of the peroxidase in human neutrophils. Biochem. Biophy. Acta. 525: 37–44.
15. Tomasz, A. 1968. Biological consequences of the replacement of choline by ethanolamine in the cell wall of pneumococcus: chain formation, loss of transformability, and loss of autolysis. Proc. Natl. Acad. Sci. U.S.A. 59: 86–93.
16. Miller, J. H. 1972. *Experiments in Molecular Genetics.* Cold Spring Harbor Laboratory, New York. pp. 137–140.
17. Amrein, P. C. and T. P Stossel. 1980. Prevention of degradation of human polymorphonuclear leukocyte proteins by diisopropylfuorophosphate. Blood 56: 442–447.
18. Shafter, W. M., L. E. Martin, and J. K. Sptiznagel. 1984. Cationic antimicrobial proteins isolated from human neutrophil granulocytes in the presence of diisopropylflourophosphate. Infect. Immun. 49: 29–35.
19. Bordier, C. 1981. Phase separation of integral membrane proteins in Triton X-114 solution. J. Biol. Chem. 256: 1604–1607.
20. Lewis, V., S. A. Green, M. Marsh, P. Vihko, A. Helenius, and I. Mellman. 1985. Glycoproteins of the lysosomal membrane. J. Cell Biol. 100: 1839–1847.
21. Geisow, M. J., P. D'Arcy Hart, and M. R. Young. 1981. Temporal changes of lysosome and phagosome pH during phagolysosome formation in macrophages: Studies by fluorescence spectroscopy. J. Cell. Biol. 89: 645–652.
22. McNeil, P. L., L. Tanasugarn, J. B. Meigs, and D. K. Taylor. 1983. Acidification of phagosomes is initiated before lysosomal enzyme activity is detected. J. Cell Biol. 97: 692–702.
23. Horwitz, M. A. and F. R. Maxfield. 1984. Legionella pneumophila inhibits acidification of its phagosome in human monocytes. J. Cell Biol. 99: 1936–1943.
24. Silverstein, S. C., R. M. Steinman and Z. A. Cohn. 1977. Endocytosis. Ann. Rev. Biochem. 46: 669–722.
25. Nikaido, H. and M. Vaara. 1985. Molecular basis of bacterial outer membrane permeability. Microbiol. Rev. 49: 1–32.
26. Chaberek, S. and A. E. Martell. 1959. Organic sequestering agents. Wiley & Sons, editors. Chapman & Hall, New York. pp. 312–313.
27. Hirsch, J. G. 1956. Phagocytin: A bactericidal substance from polymorphonuclear leucocytes. J. Exp. Med. 103: 589–611.
28. Hirsch, J. G. 1956. studies of the bactericidal action of phagocytin. J. Exp. Med. 103: 613–621.
29. Hirsch, J. G. 1960. Further studies on preparation and properties of phagocytin. J. Exp. Med. 111: 323–337.
30. Zeya, H. I. and J. K. Spitznagel. 1963. Antibacterial and enzymic basic proteins from leukocyte lysosomes: separation and identification. Science 142: 1085–1087.
31. Weiss, J., P. Elsbach, I. Olsson, and H. Odeberg. 1978. Purification and characterization of a potent bactericidal and membrane active protein from the granules of human polymorphonuclear leukocytes. J. Biol. Chem. 253: 2664–2672.
32. Elsbach, P., J. Weiss, R. C. Franson, S. Beckerdite-Quagliata, A. Schneider and L. Harris. 1979. Separation and purification of a potent bactericidal/permeability increasing protein and a closely associated phospholipase $A_2$ from rabbit polymorphonuclear leukocytes. J. Biol. Chem. 254: 11000–11009.
33. Lehrer, R. I., K. M. Ladra, and R. B. Hake. 1975. Nonoxidative fungicidal mechanisms of mammalian granulocytes: demonstration of components with candidacidal activity in human, rabbit, and guinea pig leukocytes. Infect. Immun. 11: 1226–1234.
34. Selsted, M. E., D. Szklarek, and R. I. Lehrer. 1984. Purification and antibacterial activity of antimicrobial peptides of rabbit granulocytes. Infect. Immun. 45: 150–154.
35. Gennaro, R., B. Dewald, U. Horisberger, H.-U. Gubler, and M. Baggiolini. 1983. A novel type of cytoplasmic granule in bovine neutrophils. J. Cell. Biol. 96: 1651–1661.
36. Weiss, J., T. Goldberg-Klein, and I. Olsson. 1986. Cellular and subcellular localization of the neutrophil bactericidal/permeability-increasing protein. Clin. Res. 34: 537A (Abstr.).
37. Rest, R. F., M. H. Cooney, and J. K. Spitznagel. 1978. Bactericidal activity of specific and azurophil granules from human neutrophils: studies with outer-membrane routants of Salmonella typhimurium LT-2. Infect. Immun. 19: 131–137.

38. Cohn, Z. A. and J. G. Hirsch. 1960. The isolation of the specific granules of rabbit polymorphonuclear leucocytes. J. Exp. Med. 112: 983–1003.

39. Collins, S. J., Gallo R. C., and Gallagher, R. E., 1977. Continous growth and differentiation of human myeloid leukaemic cells in suspension culture. Nature 270: 347–349.

40. Collins, S. J., Ruscetti, F. W., Gallagher, R. E., and Gallo, R. C., 1978. Terminal differentiation of human promyelocytic leukemia cells induced by dimethyl sulfoxide and other polar compounds. Proc. Natl. Acad. Sci. USA 75: 2458–2462.

41. Huynh, T. V., et al., 1984. *DNA Cloning Techniques: A Practical Approach*, Glover, D. ed., IRL, Oxford.

42. Gubler, V., et al., 1983. Gene 25: 263–269.

43. Smith, A. J. H., 1980. Meth. Enzym. 65: 560–580.

44. Ooi, C. E., et al., 1987. A 25-kDa $NH_2$-terminal Fragment Carriers All The Antibacterial Activities of the Human Neutrophil 60-kDa Bactericidal/-Permeability-Increasing Protein, J. Biol. Chem. 252: 14891–14894.hereto.

What is claimed is:

1. A purified polypeptide which is a human polymorphonuclear leukocyte polypeptide having antimicrobial activity against bacteria and fungi at a pH between 5.0 and 8.0, a predicted molecular weight of 24,832 daltons and the amino acid sequence shown in combined FIGS. 20A and 20B.

2. A purified polypeptide which is a fragment of the polypeptide of claim 1, said fragment having antimicrobial activity against bacteria and fungi at a pH between 5.0 and 8.0 and an apparent molecular weight of approximately 13,000 daltons.

3. A purified polypeptide of claim 2 having a predicted molecular weight of 12,867 daltons.

4. A purified polypeptide of claim 3 which comprises the amino acid sequence shown in combined FIGS. 20A and 20B from amino acid 105 to amino acid 220.

5. A pharmaceutical composition containing an effective bacterial or fungal killing amount of the purified polypeptide of claim 1 or 2 in a pharmaceutically acceptable carrier.

6. A purified polypeptide which is a human polymorphonuclear leukocyte polypeptide having the N-terminal amino acid sequence Ile-Val-Gly-Gly-His-Glu-Ala, an apparent molecular weight of about 29,000 daltons, respiratory burst-independent, antimicrobial activity against bacteria and fungi at a pH between 5.0 and 8.0 and at calcium ion concentrations up to 10 mM, bactericidal activity at sodium chloride concentrations up to 0.3M, and fungicidal activity at sodium chloride concentrations up to 0.15M.

7. A pharmaceutical composition containing an effective bacterial or fungal killing amount of the purified polypeptide of claim 6 in a pharmaceutically acceptable carrier.

* * * * *